United States Patent [19]
Doll et al.

[11] Patent Number: 5,880,128
[45] Date of Patent: Mar. 9, 1999

[54] CARBONYL PIPERAZINYL AND PIPERIDINYL COMPOUNDS

[75] Inventors: Ronald J. Doll, Maplewood; Alan K. Mallams, Hackettstown; Adriano Afonso, West Caldwell; Dinanth F. Rane, Morganville; George F. Njoroge, Union; Randall R. Rossman, Nutley, all of N.J.; John J. Baldwin, Gwynedd Valley, Pa.; Ge Li, Englewood; John C. Reader, Princeton, both of N.J.

[73] Assignees: Schering Corporation, Kenilworth; Pharmacopeia Inc., Princeton, both of N.J.

[21] Appl. No.: 646,835

[22] Filed: May 8, 1996

[51] Int. Cl.$^6$ .................. C07D 295/18; A61K 31/495
[52] U.S. Cl. .................. 514/255; 544/359; 544/360; 544/361; 544/362; 544/363
[58] Field of Search .................. 544/359, 360, 544/361, 362, 363; 514/255

[56] References Cited

U.S. PATENT DOCUMENTS

| | | | |
|---|---|---|---|
| 3,576,810 | 4/1971 | Duncan et al. | 260/294 |
| 4,921,863 | 5/1990 | Sugimoto et al. | 514/319 |
| 5,202,346 | 4/1993 | Butera et al. | 514/326 |
| 5,231,105 | 7/1993 | Shoji et al. | 514/325 |
| 5,384,319 | 1/1995 | Ferrini | 514/227.8 |

FOREIGN PATENT DOCUMENTS

| | | |
|---|---|---|
| 235752 | 9/1987 | European Pat. Off. . |
| 9500497 | 1/1995 | WIPO . |
| 9606609 | 3/1996 | WIPO . |
| 9610035 | 4/1996 | WIPO . |

OTHER PUBLICATIONS

Chemical Abstracts No. 100:203138 & Registry No. 90126–04–8 of Shiozawa et. al., Chem. Pharm. Bull. (1984), vol. 32, No. 2, pp. 553–563.

*Primary Examiner*—Jose G. Dees
*Assistant Examiner*—Sabiha Qazi
*Attorney, Agent, or Firm*—Joseph T. Majka

[57] ABSTRACT

Novel carbonyl piperazinyl and piperidinyl compounds and pharmaceutical compositions are disclosed. Also disclosed is a method of inhibiting Ras function and therefore inhibiting the abnormal growth of cells. The method comprises administering the novel carbonyl piperazinyl or piperidinyl compound to a biological system. In particular, the method inhibits the abnormal growth of cells in a mammal such as a human being.

11 Claims, No Drawings

CARBONYL PIPERAZINYL AND PIPERIDINYL COMPOUNDS

BACKGROUND

Patent application WO 95/00497 published 5 Jan. 1995 under the Patent Cooperation Treaty (PCT) describes compounds which inhibit farnesylprotein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

The present invention is directed to novel carbonyl piperazinyl and piperidinyl compounds of the formula:

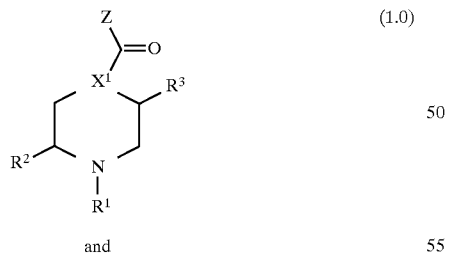

(1.0)

and

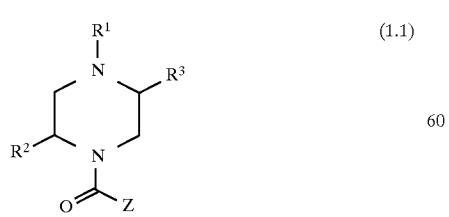

(1.1)

or a pharmaceutically acceptable salt or solvate thereof, wherein:

(1) Z is a group which is:

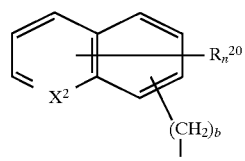

(-i-)

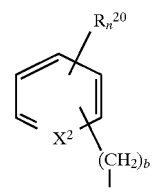

(-ii-)

or

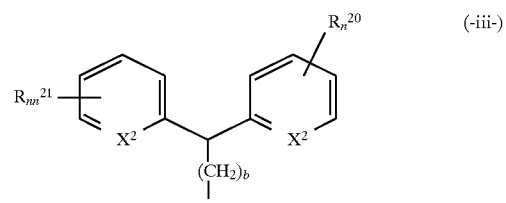

(-iii-)

wherein $X^1$ is CH or N;

$X^2$ can be the same or different and can be CH, N or N—O;

b is 0, 1, 2, 3 or 4;

n and nn independently represent 0, 1, 2, 3, 4 or when $X^2$ is CH, n and nn can be 5;

$R^{20}$ and $R^{21}$ can be the same group or different groups when n or nn is 2, 3, 4 or 5, and can be:

(a) hydrogen, $C_1$ to $C_6$ alkyl, aryl, aralkyl, heteroaryl, heteroarylalkyl or heterocycloalkyl, wherein each of said $C_1$ to $C_6$ alkyl, aryl, aralkyl, heteroaryl, heteroarylalkyl or heterocycloalkyl can be optionally substituted with one or more of the following:

$C_1$ to $C_4$ alkyl, $C_3$–$C_6$ cycloalkyl,
$(CH_2)_tOR^8$ wherein t is 0, 1, 2, 3 or 4,
$(CH_2)_tNR^8R^9$ wherein t is 0, 1, 2, 3 or 4, or halogen;

(b) $C_3$ to $C_6$ (c) —$OR^8$; (d) —$SR^8$; (e) —$S(O)R^8$; cycloalkyl; (f) —$SO_2R^8$; (g) —$NR^8R^9$; (h) —CN; (i) —$NO_2$, (j) —$CF_3$ or (k) halogen (l) —$CONR^8R^9$ or (m) —$COR^{13}$ wherein $R^8$ and $R^9$ can independently represent:

H, $C_1$ to $C_4$ alkyl, $C_3$ to $C_6$ cycloalkyl, heteroaryl, heteroarylalkyl, heterocycloalkyl, aryl or aralkyl and each of said alkyl, cycloalkyl, heteroaryl, heteroarylalkyl, heterocycloalkyl, aryl or aralkyl can be optionally substituted with one to three of the following:

$C_1$ to $C_4$ alkoxy, aryl, aralkyl, heteroaryl, heteroarylalkyl, heterocycloalkyl, halogen, —OH, —$C(O)R^{13}$, —$NR^{14}R^{15}$;
—$CONR^8R^9$ or —$N(R^8)COR^{13}$; —CN; $C_3$–$C_6$ cycloalkyl, $S(O)_qR^{13}$;
or $C_3$–$C_{10}$ alkoxyalkoxy wherein q is 0, 1 or 2;
wherein $R^{13}$ is selected from $C_1$ to $C_4$ alkyl, aryl or aralkyl, and
$R^{14}$ and $R^{15}$ are independently selected from H, $C_1$ to $C_4$ alkyl or aralkyl;

and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, $S(O)q$ wherein q is 0, 1 or 2;

with the proviso that $R^8$ is not H in substituents (e) and (f), and with the proviso that $R^8$ or $R^9$ is not —$CH_2OH$ or —$CH_2NR^{14}R^{15}$ when $R^8$ or $R^9$ is directly attached to a heteroatom;

(2) $R^1$ is a group which is:

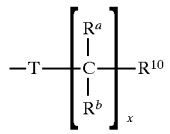

wherein
T can be

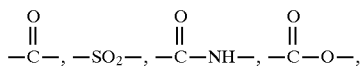

or a single bond, x=0, 1, 2, 3, 4, 5 or 6, $R^a$ and $R^b$ independently represent H, aryl, alkyl, amino, alkylamino, alkoxy, aralkyl, heterocyloalkyl, —$COOR^{16}$, —$NH(CO)_zR^{16}$ wherein z=0 or 1, —$(CH_2)_wS(O)_mR^{16}$ wherein w=0, 1, 2 or 3 such that when x is greater than 1, then $R^a$ and $R^b$ can be independent of the substituents on an adjacent carbon atom provided $R^a$ and $R^b$ are not both selected from alkoxy, amino, alkylamino, and —$NH(CO)_zR^{16}$;

m=0, 1 or 2 wherein $R^{16}$ represent H, alkyl, aryl or aralkyl, or $R^a$ and $R^b$ taken together can represent cycloalkyl, =O, =N—O-alkyl or heterocycloalkyl, and $R^{10}$ can represent H, alkyl, aryl, aryloxy, arylthio, aralkoxy, aralkthio, aralkyl, heteroaryl, heterocycloalkyl, or $R^1$ can also be

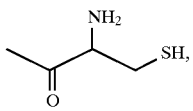

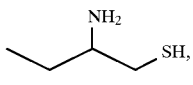

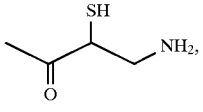

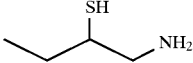

or disulfide dimers thereof;

(3) $R^2$ and $R^3$ are independently selected from the group which is:

hydrogen, $C_1$ to $C_8$ alkyl, $C_2$ to $C_8$ alkenyl, $C_2$ to $C_8$ alkynyl,

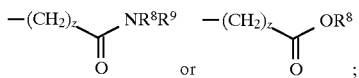

wherein z is 0, 1, 2, 3 or 4; and said alkyl, alkenyl, or alkynyl group is optionally substituted with one or more groups which can independently represent:

(a) aryl, aralkyl, heteroaryl, heteroarylalkyl or heterocycloalkyl, wherein each of said aryl, aralkyl, heteroaryl, heteroarylalkyl or heterocycloalkyl group can be optionally substituted with one or more of the following:

$C_1$ to $C_4$ alkyl, $(CH_2)_tOR^8$ wherein t is 0, 1, 2, 3 or 4, $(CH_2)_tNR^8R^9$ wherein t is 0, 1, 2, 3 or 4, or halogen;

(b) $C_3$ to $C_6$ (c) —$OR^8$; (d) —$SR^8$; (e) —$S(O)R^8$; cycloalkyl; (f) —$SO_2R^8$; (g) —$NR^8R^9$;

                                  (h)

                                  (i)

                                 (j)

                                 (k)

                                 (l)

                                 (m)

                                 (n)

                                 (o)

or

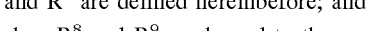                                 (p)

wherein $R^8$ and $R^9$ are defined hereinbefore; and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, $S(O)q$ wherein q is 0, 1 or 2;

with the proviso that for compound (1.0) when $X^1$ is CH, then $R^3$ is hydrogen, and with the further proviso that $R^2$ and $R^3$ cannot both be hydrogen; and with the provision that when $X^1$ is N, then $R^1$ is not

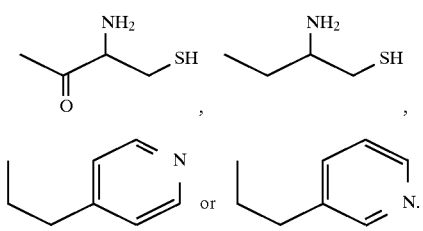

One skilled in the art will recognize that compound (1.0) and (1.1) are identical when $R^2$ and $R^3$ are the same. One skilled will also recognize that compounds (1.0) and (1.1) are positional isomers when $R^2$ is different from $R^3$. In the present specification, the procedures described herein for preparing compound (1.0) are also applicable for preparing compound (1.1).

Preferably, $R^3$ is H; b is 0; or $R^3$ is H and b is 0.

Also preferred is that Z is (—i—), (—ii—) or (—iii—), $X^2$ is CH or N, b=0 or 1, $R^{20}$ is H, $C_1$–$C_6$ alkyl or halo, n=0 or 1;

$X^1$ is N;

for $R^1$, T is —CO—, —SO$_2$— or a single bond, and $R^a$ and $R^b$ independently represent H or $C_1$–$C_6$ alkoxy or $R^a$ and $R^b$ taken together can form $C_3$–$C_6$ cycloalkyl, =N—O—

C1–C6 alkyl or

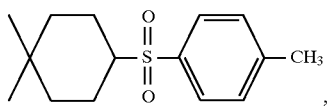

$R^{10}$ is H, aryl, arylthio or heteroaryl;
$R^2$ is H,

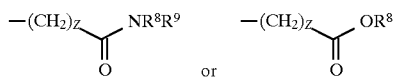

z=0 or 1, $R^8$ is H and $R^9$ is alkyl, cycloalkyl, aralkyl, heterocycloalkyl or substituted alkyl; and $R^3$ is hydrogen.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the carbonyl piperazinyl and piperidinyl compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the carbonyl piperclzinyl and piperidinyl compounds (1.0) described herein.

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

Ac—represents acetyl;

acyl radical of a naturally occurring amino acid—represents a group of the formula —C(O)C(NH$_2$)$R^{26}R^{28}$, i.e.:

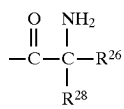

wherein $R^{26}$ and $R^{28}$ represent the substituents of an amino acid bound to the α-carbon; for example $R^{26}$ and $R^{28}$ can be independently selected from H, alkyl, or alkyl substituted with an $R^{30}$ group, wherein $R^{30}$ can be, for example, —OH, SH, —SCH$_3$, —NH$_2$, phenyl, p-hydroxyphenyl, indolyl or imidazolyl, such that HO—C(O)C(NH$_2$)$R^{26}R^{28}$ is an amino acid selected from, for example, alanine, cysteine, cystine, glycine, histidine, isoleucine, leucine, lysine, methionine, phenylalanine, serine, tryptophane, tyrosine or valine. Preferably the stereochemistry of the amino acid is of the L absolute configuration.

alkyl—(including the alkyl portions of alkoxy, alkylamino and dialkylamino)—represents straight and branched carbon chains and contains from one to twenty carbon atoms, preferably one to six carbon atoms; for example methyl, ethyl, propyl, iso-propyl, n-butyl, t-butyl, n-pentyl, isopentyl, hexyl and the like; wherein said alkyl group may be optionally and independently substituted with one two or three of hydroxy, alkoxy, halo (e.g. CF$_3$), amino, alkylamino, dialkylamino, N-acylalkylamino, N-alkyl-N-acylamino, —S(O)$_m$-alkyl where m=0, 1 or 2 and alkyl is defined above;

alkoxy-an alkyl moiety of one to 20 carbon atoms covalently bonded to an adjacent structural element through an oxygen atom, for example, methoxy, ethoxy, propoxy, butoxy, pentoxy, hexoxy and the like.

alkenyl—represents straight and branched carbon chains having at least one carbon to carbon double bond and containing from 2 to 12 carbon atoms, preferably from 2 to 6 carbon atoms and most preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aq—represents aqueous aralkyl—represents an alkyl group, as defined above, wherein one or more hydrogen atoms of the alkyl moiety have been replaced by one or more aryl groups, as defined below (e.g., benzyl, diphenylmethyl);

aryl (including the aryl portion of aryloxy and aralkyl)- represents a carbocyclic group containing from 6 to 15 carbon atoms and having at least one aromatic ring (e.g., aryl is phenyl or napthyl), with all available substitutable carbon atoms of the carbocyclic group being intended as possible points of attachment, said carbocyclic group being optionally and independently substituted with one, two, three or more of halo, C1–C6 alkyl, C1–C6 alkoxy, amino, alkylamino, dialkylamino, aryl, aralkoxy, aryloxy, —NO$_2$, —S(O)$_m$-aryl wherein m=0, 1 or 2, C(O)$R^{11}$ (wherein R11 is as defined hereinbefore), an acyl radical, —COO$R^{16}$ (wherein $R^{16}$ represents H, alkyl, aryl or aralkyl), or substituted C1–C6 alkyl wherein the alkyl group is substituted with one two or three of amino, alkylamino, dialkylamino, aryl, N-acylalkylamino, N-alkyl-N-acylamino, N-aralkyl-N-acylamino, hydroxy, alkoxy, halo, or heterocycloalkyl, provided that when there are two or more hydroxy, amino, alkylamino or dialkylamino substituents on the substituted C$_1$–C$_6$ alkyl group, the substituents are on different carbon atoms; or alternatively said aryl group may be fused through adjacent atoms to form a fused ring containing up to four carbon and/or heteroatoms (e.g. methylene dioxyphenyl, indanyl, tetralinyl, dihydrobenzofuranyl);

aralkoxy—represents an aralkyl group, as defined above, in which the alkyl moiety is covalently bonded to an adjacent structural element through an oxygen atom, e.g. benzyloxy;

aryloxy—represents an aryl group, as defined above, covalently bonded to an adjacent structural element through an oxygen atom, e.g, phenoxy;

arylthio—represents an aryl group, as defined above, covalently bonded to an adjacent structural element through a sulfur atom, for example, phenylthio;

BOC—represents tert-butoxycarbonyl;

BOC-ON—represents [2-(tert-butoxycarbonyloxyimino) -2-phenylacetonitrile];

C—represents carbon;

CBZ—represents benzyloxycarbonyl;

CPh$_3$—represents triphenylmethyl;

cycloalkyl—represents a saturated carbocyclic ring, branched or unbranched, of from 3 to 20 carbon atoms, preferably 3 to 7 carbon atoms;

DBU—represents 1,8-diazabicyclo[5.4.0]undec-7-ene;

DCC—represents dicyclohexylcarbodiimide;

DCM—represents dichloromethane;

DIC—represents diisopropylcarbodiimide;

DMAP—represents 4-dimethylaminopyridine;

DMF—represents N,N-dimethylformamide;

EDC (also DEC)—represents 1-(3-dimethylaminopropyl) -3-ethylcarbodiimide hydrochloride or 1-ethyl-3-(3-dimethylaminopropyl)carbodiimide hydrochloride;

FMOC—represents 9-fluorenylmethyoxycarbonyl;

FMOC-Cl—represents 9-fluoroenylmethyl chloroformate;

HATU—represents [O-(7-azabenzotriazol-1-yl)-1,1,3,3-tetramethyluronium hexafluorophosphate];

MCPBA—represents m-chloroperbenzoic acid;

Ph—represents phenyl;

TBAF—represents tetrabutylammonium fluoride;

TFA—represents trifluoroacetic acid;

THF—represents tetrahydrofuran;

halogen (halo)—represents fluoro, chloro, bromo and iodo;

haloalkyl—represents an alkyl group, as defined above, wherein one or more hydrogen atoms have been replaced by one or more halogen atoms, ie. chloromethyl and trifluromethyl;

heterocycloalkyl—represents a saturated, branched or unbranched mono-, bi- or tricyclic carbocylic ring(s) containing from 3 to 15 carbon atoms in each ring, preferably from 4 to 6 carbon atoms, wherein at least one carbocyclic ring is interrupted by 1 to 3 heteroatoms selected from —O—, —S— or —N— (suitable heterocycloalkyl groups include 2- or 3-tetrahydrofuranyl, 2- or 3-tetrahydrothienyl, 2-, 3- or 4-piperidinyl, 2- or 3-pyrrolidinyl, 1-,2- or 3-morpholino, 2- or 3-piperizinyl, 2- or 4-dioxanyl, diaza-2,2,2-bicyclooctane etc.); with any of the available substitutable carbon and nitrogen atoms in the ring being optionally and independently substituted with one, two, three or more of $C_1$–$C_6$ alkyl, aryl, aralkyl, haloalkyl, amino, alkylamino, dialkylamino, —S(O)$_m$-aryl where m=0, 1 or 2 and aryl is defined above, —C(O)R$^{11}$ wherein R$^{11}$ is defined above or an acyl radical of a naturally occuring amino acid;

heteroaryl—represents cyclic groups having one, two or three heteroatom selected from —O—, —S— or —N—, said heteroatom interrupting a carbocyclic ring structure and having a sufficient number of delocalized pi electrons to provide aromatic character, with the aromatic heterocyclic groups preferably containing from 2 to 14 carbon atoms, e.g., quinolinyl, imidazolyl, furanyl, triazolyl, thiazolyl, indolyl, benzothienyl, 2- or 3- thienyl, 1-, 2-, 3- or 4-pyridyl or pyridyl N-oxide, wherein pyridyl N-oxide can be represented as:

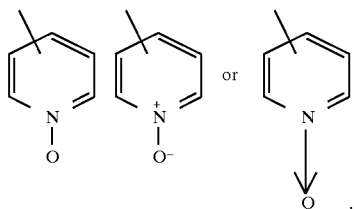

with all available substitutable carbon and heteroatoms of the cyclic group being intended as possible points of attachment, said cyclic group being optionally and independently substituted with one, two, three or more of halo, alkyl, aryl, aralkyl, heteroaryl, hydroxy, alkoxy, phenoxy, —NO$_2$, CF$_3$, amino, alkylamino, dialkylamino, and —COOR$^{16}$ wherein R$^{16}$ represents H, alkyl, aryl or aralkyl (e.g., benzyl);

heteroarylalkyl—represents an alkyl group, as defined above, wherein one or more hydrogen atoms have been replaced by heteroaryl groups (as defined above);

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain compounds (1.0) will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds (1.0) can also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia or sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following processes may be employed to produce compounds of the invention. Various intermediates in the processes described below can be produced by methods known in the art, see for example, U.S. Pat. No. 3,409,621, U.S. Pat. No. 5,089,496, WO89/10369, WO92/20681, and WO93/02081, the disclosures of each being incorporated herein by reference thereto.

A. Process A for Preparing Piperazinyl Compounds and Starting Materials.

The piperazinyl compounds of the present invention and starting materials thereof, can be prepared according to the following overall Process A.

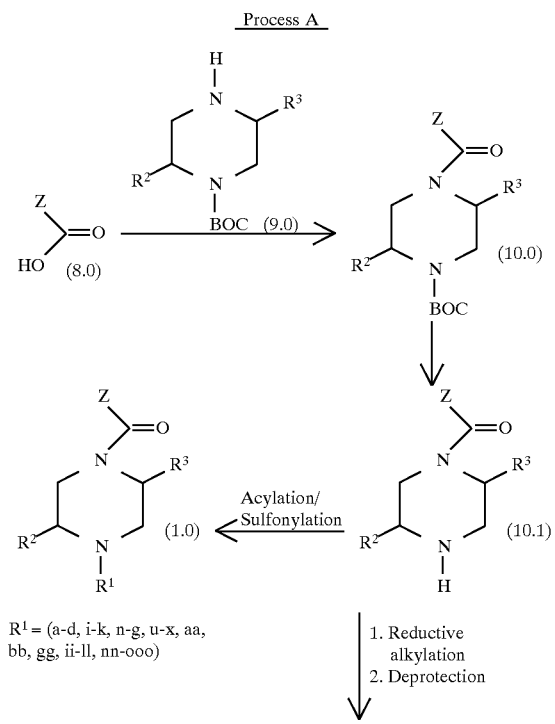

-continued
Process A

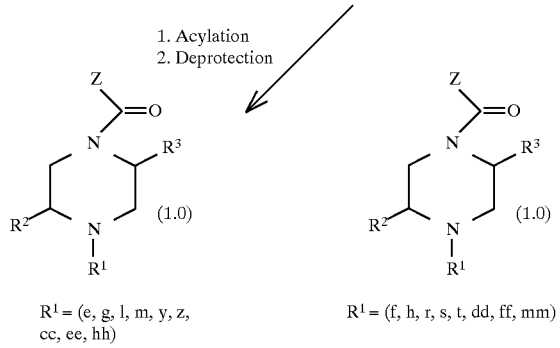

$R^1$ = (e, g, l, m, y, z, cc, ee, hh)   $R^1$ = (f, h, r, s, t, dd, ff, mm)

wherein Z, BOC, $R^1$, $R^2$ and (a-ooo) are as defined herein.

A1. Preparation of Piperazinyl Starting Materials.

The aromatic compounds ("Z") of formula (3.0)

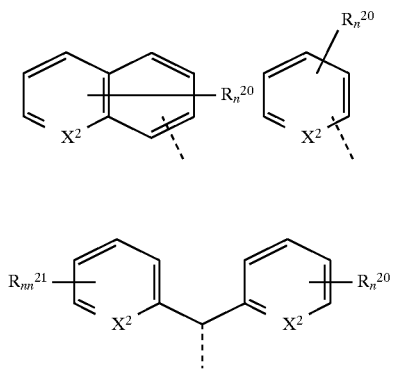

wherein $R_n^{20}$, $R_{nn}^{21}$ and $X^2$ are as defined hereinbefore, and the solid floating bond indicates that $R_n^{20}$ and $R_{nn}^{21}$ can be bonded to the aromatic ring at any suitable atom for attachment, ie.carbon, are known to those skilled in the art. The dotted floating bond indicates the subsequent site of introduction for the carboxyl group.

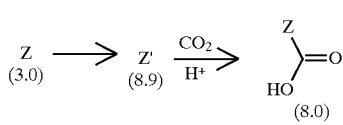

Using a reaction such the Kolbe-Schmidt Reaction, the carboxylic acids of formula (8.0) can be prepared by contacting the aromatic compounds of formula (3.0) with a base such as n-butyl lithium, followed by treatment with carbon dioxide, followed then by treatment with a suitable acid, such as hydrochloric acid, to give carboxylic acid (8.0), which are also compounds known in the art.

Alternatively, carboxylic acid (8.0), wherein b=0, can be prepared by reacting the aromatic halide (i.e.$R^{20}$ is halo) of compound (3.0) and an organometallic such as n-butyl lithium to yield aromatic anion (8.9), which is then treated with carbon dioxide and acid as described above, to give carboxylic acid (8.0).

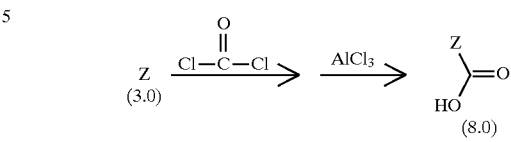

In an alternative reaction, carboxylic acids (8.0) can be prepared by reacting aromatic compounds (3.0) with phosgene in the presence of a Lewis Acid, such as aluminum chloride ($AlCl_3$) followed by hydrolysis of the acid chloride to give carboxylic acid (8.0).

Also, carboxylic acids (8.0) wherein b=1, 2, 3 or 4 are also known in the art, e.g. 3-pyridylacetic acid, 3-phenylpropionic acid, 4-phenylbutyric acid and the like.

The carboxylic acid (8.0) is then reacted with piperazinyl intermediate (9.0) in the presence of a coupling reagent (such as a carbodiimide, e.g., dicyclohexylcarbodiimide) in a suitable solvent such as DMF at a suitable temperature to produce the piperazinyl amide (10.0).

The preparation of compounds of Formula 9.0 is described in WO 95/00497, published Jan. 5, 1995, the disclosure of which is incorporated herein by reference thereto. The preparation of piperazinyl intermediate (9.0) is depicted in Schemes 1 and 2.

SCHEME 1

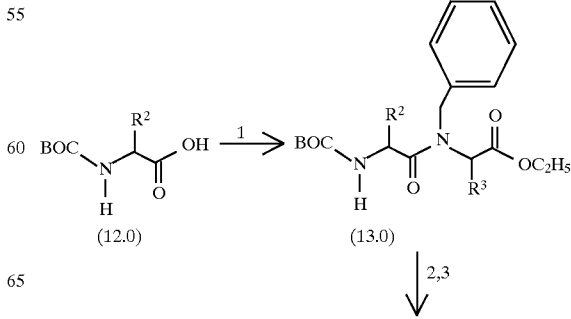

SCHEME 1 -continued

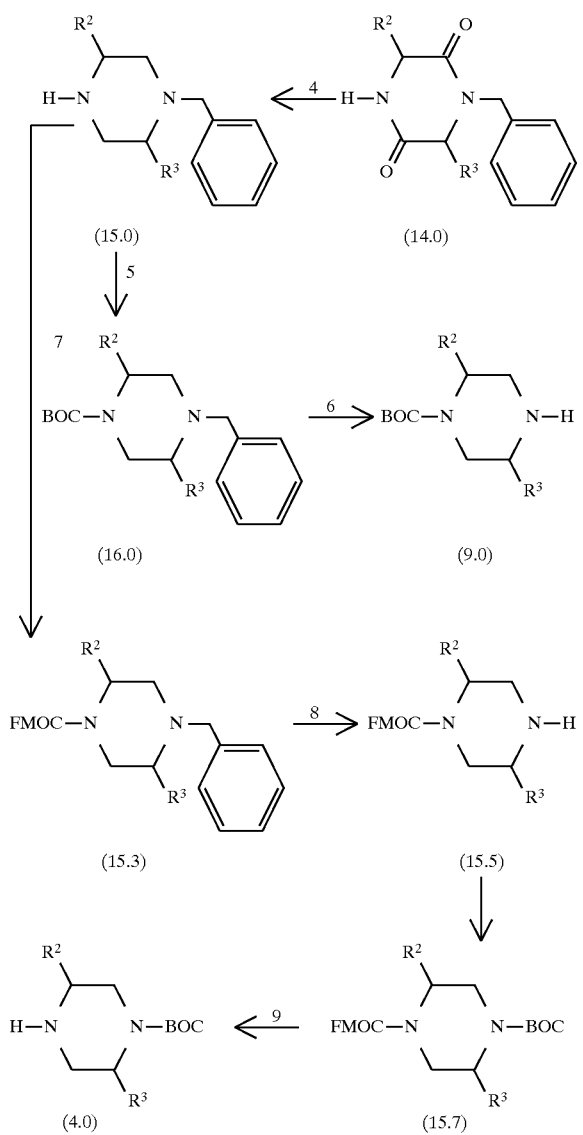

Scheme 1 describes the synthesis of 2,3-disubstituted piperazines wherein $R^2$ and $R^3$ independently represent H, alkyl, alkenyl, or alkynyl. Scheme 1 also describes the synthesis of 2,3-disubstituted piperazines wherein $R^2$ and $R^3$ independently represent is alkyl, alkenyl, or alkynyl which are substituted with substituent groups (a), (b), (c), (d) and (g) as defined above, with the exception that $R^8$ and $R^9$ cannot be a group that is substituted with $-C(O)R^{13}$ or $-SO_2R^{13}$. In Scheme 1, BOC-protected amino acids (12.0) are available commercially or can be made by procedures well known in the art. These amino acids can be coupled (step 1) to a commercially availble N-benzylprotected amino acid, ethyl ester using suitable coupling agents such as DCC or EDC in suitable solvents (e.g., N, N-dimethylformamide, chloroform or methylene chloride) to produce a compound of Formula 13.0. Generally, this reaction is conducted at room temperature (i.e., about 25° C.). The BOC protecting group is removed (step 2) at room temperature with suitable reagents such as trifluoroacetic acid, or hydrogen chloride in chloroform or dioxane. The deprotected dipeptide is cyclized (step 3) under basic conditions to produce the compound of Formula 14.0. The compound of Formula 14.0 is then reduced (step 4) using $LiAlH_4$ in refluxing ether (diethyl ether) or THF to give the piperazine of Formula 15.0. The unsubstituted nitrogen of the piperazine of Formula 15.0 is protected (step 5) with a BOC group by procedures well known in the art to give the compound of Formula 16.0. The N-benzyl group is removed (step 6) by catalytic hydrogenation (e.g., using Pd/C and hydrogen gas under pressure of about 60 psi) to give the compound of Formula (9.0). Alternatively, compound (15.0) can be converted to the FMOC derivative (15.3) by treatment with FMOC-Cl in the presence of a base such as sodium bicarbonate in an aqueous dioxane. The FMOC derivative (15.3) can be debenzylated as described in step 6 above, to give compound (15.5). Compound (15.5) can be converted to the BOC-derivative (15.7) by procedures known in the art. Compound (15.7) can be converted to compound (4.0) by heating in a suitable hydroxyl solvent such as methanol.

Those skilled in the art will appreciate that the compound of Formula 9.0 can exist as the following enantiomers

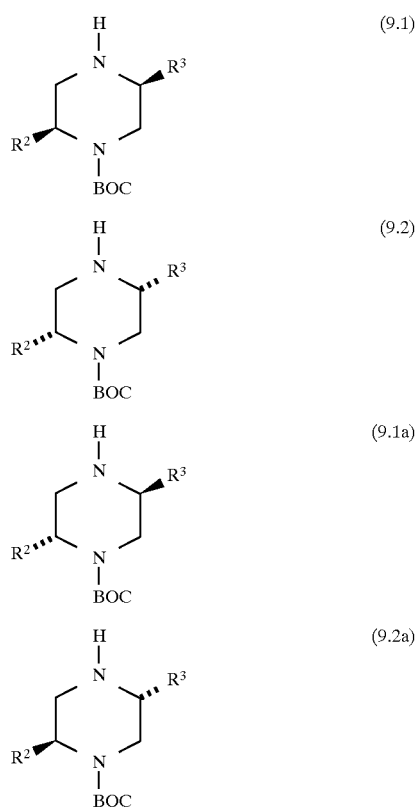

These piperazinyl isomers yield the desired isomers of compound (1.0) shown below:

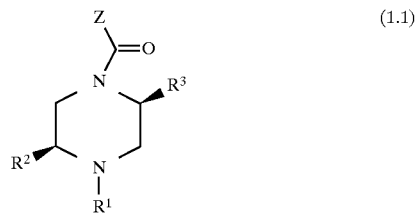

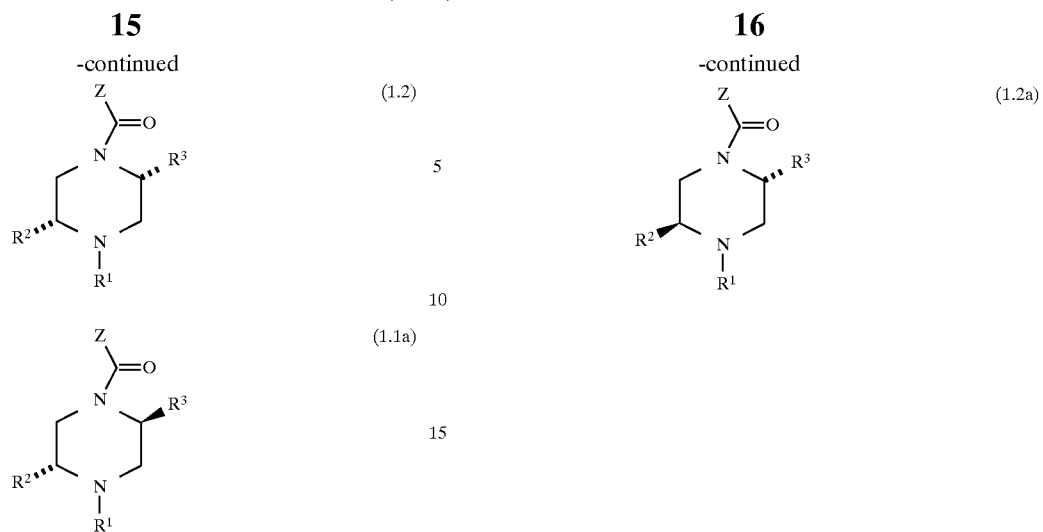
SCHEME 2
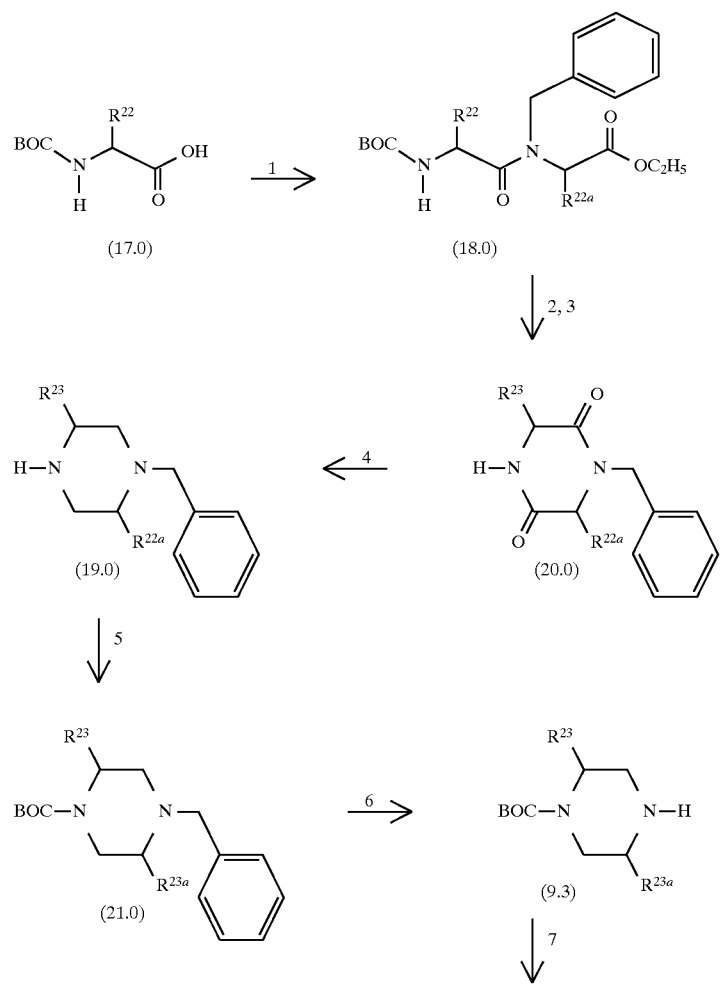

-continued
SCHEME 2

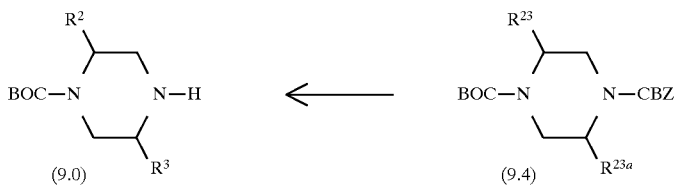

Compounds (9.0), wherein $R^2$ and $R^3$ independently represent alkyl, alkenyl or alkynyl substituted with (a), (c), (d) or (g) groups wherein $R^8$ or $R^9$ are substituted with —C(O)$R^{13}$ or —S(O)$_2R^{13}$ are made according to the process of Scheme 2. Compounds (9.0), whererin $R^2$ and $R^3$ independently represent represent —C(O)NR$^8R^9$ or —C(O)OR$^8$, or wherein $R^2$ and $R^3$ independently represent alkyl, alkenyl or alkynyl substituted with its groups (e), (f), or (h)–(p) are also made according to the process of Scheme 2. Compounds (17.0) and (18.0), wherein $R^{22}$ and $R^{22}$a independently represent alkyl, alkenyl or alkynyl group containing either a —OH group, a —COOH or its corresponding ester, are available commercially or can be made by procedures known in the art. In Scheme 2, the compound (17.0) is reacted according to the procedures described for Scheme 1 (steps 1 to 4) to produce a compound (19.0) wherein $R^{23}$ and $R^{23a}$ independently represent a hydroxy substituted alkyl, alkenyl or alkynyl group. The compound (19.0) is then protected with a BOC group and then debenzylated according to the procedures in Scheme 1 (Steps 5 and 6) to produce a compound (9.3). The unsubstituted nitrogen of compound (9.3) is protected (step 7) with a CBZ group by procedures known in the art to produce the compound (9.4). The groups $R^{23}$ and $R^{23a}$ on compound (9.4) can be converted to $R^2$ and $R^3$, respectively, followed by deprotection of compound (9.4) by catalytic hydrogenation, i.e. palladium/carbon and hydrogen in a suitable solvent such as methanol, to give compound (9.0).

When $R^{23}$ and $R^{23a}$ of compound (9.4) is —CH$_2$OH, the hydroxy group can be oxidized to produce the corresponding carboxyl group—(COOH). This carboxyl group can them be esterified to produce compounds wherein $R^2$ is —C(O)OR$^8$, or the carboxyl group can be converted to amides to produce compounds wherein $R^2$ or $R^3$ are —C(O)NR$^8R^9$ by procedures well known in the art.

To produce compounds (9.0) in Scheme 2 wherein $R^2$ and/or $R^3$ is a substituent other than —C(O)OR$^8$ or —C(O)NR$^8R^9$, the hydroxy group on $R^{23}$ or $R^{23a}$ in compound (9.4) can be converted to a leaving group, such as chloro, mesyloxy or tosyloxy, by techniques well known in the art. Then the leaving group can be displaced by various nucleophiles such as organometallics (to produce $R^2$ and/or $R^3$ with an (a) substituent), thiols (to produce $R^2$ and/or $R^3$ with a (d) substituent), sulfenyls (to produce $R^2$ and/or $R^3$ with an (e) substituent), sulfinyls (to produce $R^2$ and/or $R^3$ with an (f) or (m) substituent), amines (to produce $R^2$ and/or $R^3$ with a (g) substituent), and alcohols (to produce $R^2$ and/or $R^3$ with a (c) substituent). The hydroxy group on $R^{23}$ and/or $R^{23a}$ in compound (9.4) can also be acylated (to produce $R^2$ and/or $R^3$ with a (j) or (k) substituent) or alkylated (to produce $R^2$ and/or $R^3$ with a (c) substituent). When $R^{23}$ and/or $R^{23a}$ in compound (9.4) is alkyl having more than one carbon atom, or alkenyl or alkynyl, the hydroxy group can be oxidized, as discussed above, to produce the corresponding carboxyl group (i.e., substituent (o) wherein $R^8$ is H). This carboxyl group can be esterified to produce compounds wherein substituent (o) is —C(O)OR$^8$ wherein $R^8$ is other than H, or converted to amides to produce to produce $R^2$ and/or $R^3$ with an (l) substituent by procedures well known in the art. When the leaving group is displaced by an amine (e.g., —NR$^8R^9$), the amine can then be converted to $R^2$ and/or $R^3$ substituent groups (h), (i) or (n) by reacting the amine with an acyl halide (to produce $R^2$ and/or $R^3$ with an (h) substituent), a carbamyl halide (to produce $R^2$ and/or $R^3$ with an (i) substituent) or a sulfonyl halide (to produce $R^2$ and/or $R^3$ with an (n) substituent) by procedures well known in the art, which following deprotection, give compound (9.0).

The compound of Formula 10.0 can be deprotected (i.e., the BOC group removed) by treatment with an acid (e.g. trifluoroacetic acid, or HCl-dioxane) to produce the compound (10.1).

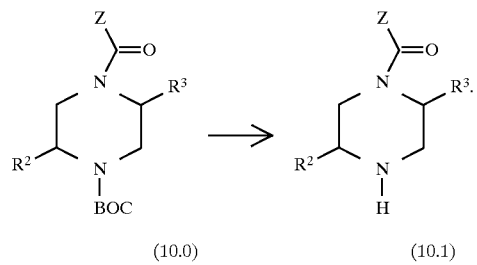

A2. Preparation of Piperazinyl Compounds.

Compound (10.1) can be converted to the desired piperazinyl compound (1.0), wherein $X^1$ is N, by acylation, acylation and deprotection or reductive alkylation, optionally with deprotection.

Acylation of the compound (10.1) can be carried out by reacting it with a compound having a carboxylic acid moiety contained in or part of the desired $R^1$ group, with a coupling agent, such as a carbodiimide such as dicyclohexylcarbodiimide(DCC) or DEC (1-ethyl-3-(3-dimethylaminopropyl)carbodiimide). The acylation reaction can be carried out in a suitable organic solvent such as DMF, THF or methylene chloride at a temperature of about −10° to about 100° C., preferably at about 0° to about 50° C., and most preferably about room temperature. When the coupling reagent is DCC or DEC, the reaction is preferably conducted in the presence of HOBT.

Compounds (1.0), wherein $R^1$ is a substituent (a-e, g, i-q, u-cc, ee, gg-ll, nn-ooo) can be made by reacting a compound (10.1) with $R^1$-L, wherein $R^1$ contains the —C(O)— group and L is a leaving group such as Cl, Br, I, or a carboxylate (an anhydride). The reaction is carried out in the presence of a base, preferably a tertiary amine such as triethylamine or N-methyl morpholine.

Specifically, compounds (1.0) wherein $R^1$ is a substituent (u) to (y) can be made by reacting a compound of Formula (10.1) or (30.0) with a pyridyl chloroformate or piperidyl chloroformate; or, alternatively, reacting a compound (10.1) or (30.0) with excess phosgene and reacting the chloroformate thus produced with a hydroxypyridyl N-oxide or hydroxypiperidine derivative. The reaction is carried out in a suitable solvent, such as dichloromethane, in the presence of a tertiary amine, such as pyridine, by techniques well known in the art.

Alternatively, compounds (1.0), wherein $R^1$ is a substituent (m) to (q) can be made by reacting a compound (10.1) with a pyridyl isocyanate, pyridyl N-oxide isocyanate or piperidyl isocyanate corresponding to the pyridyl, pyridyl N-oxide or piperidyl moiety, respectively, of the substituent groups (m) to (q). The reaction is carried out in a suitable solvent such as DMF, THF or chloroform using techniques well known in the art. Alternatively, these ureas can be prepared by reacting a compound (10.1) with phosgene to form a chloroformate intermediate ($R^1$ is —C(O)Cl). This chloroformate is generally not isolated, and is reacted with pyridyl amine, pyridyl N-oxide amine or piperidyl amine corresponding to the pyridyl, pyridyl N-oxide or piperidyl moiety, respectively, of the substituent groups (m) to (q) by techniques well known in the art.

When compounds of Formulas 10.1 ($X^1$ is N) or 30.0 ($X^1$ is CH) are acylated to make the compounds (1.0) wherein $R^1$ is substituents (g) or (e), the protected compounds of Formulas 32.0 and 33.0, respectively are formed.

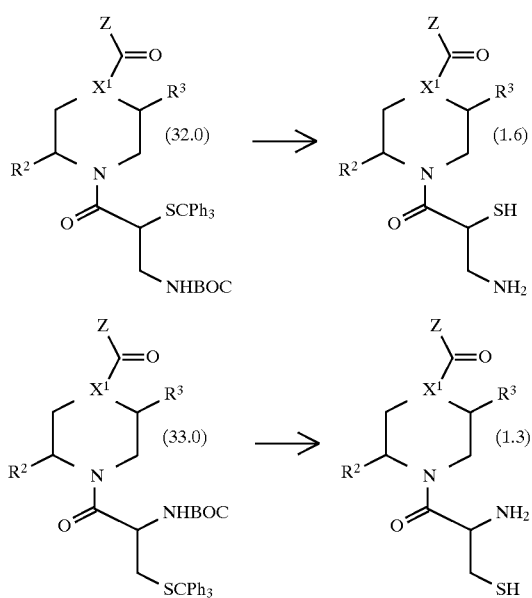

Protected compounds (32.0) and (33.0) can be deprotected by using trifluoroacetic acid and triethylsilane to yield compounds (1.6) and (1.3), respectively, which are isolated as the hydrochloride salts.

Reductive alkylation (i.e. reductive amination) of compound (10.1) can be accomplished by reacting compound (10.1) with an aldehyde in DMF with a dehydrating agent such as molecular sieves at room temperature (about 25° C.). This reaction is followed by reduction of the intermediate imine with a reducing agent such as sodium cyanoborohydride or sodium triacetoxyborohydride. The reduction is usually carried out at room temperature in a suitable solvent such as DMF.

When compounds of Formulas 10.1 ($X^1$ is N) or 30.0 ($X^1$ is CH) are reductively alkylated to make the compounds (1.0) wherein $R^1$ is substituents (h) or (f), the protected compounds (34.0) and (35.0), respectively are formed.

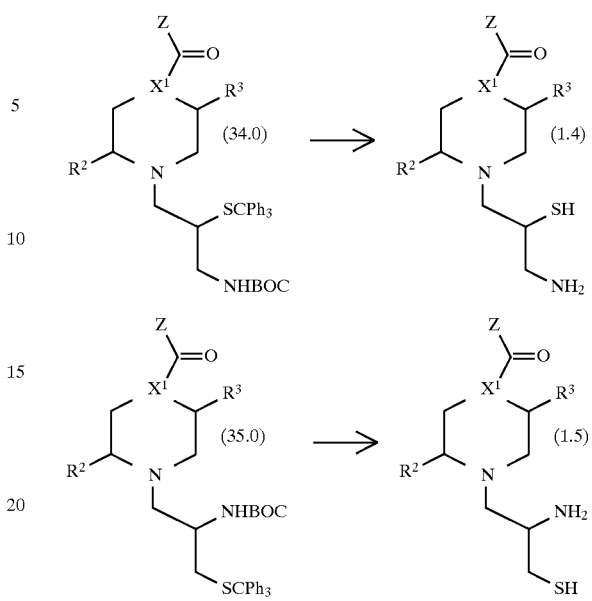

These protected compounds can be deprotected by using trifluoroacetic acid and triethylsilane to give, respectively, compounds (1.4) and (1.5) which are isolated as the hydrochloride salts.

Compounds of Formula (1.0) wherein $R^1$ is a substitutent (u) to (y) can be made by reacting a compound $R^1$—Cl, wherein $R^1$ is a substituent (u) to (y), with a compound of Formula 10.1 or 30.0, in dichloromethane with a tertiary amine base. The reaction is conducted at about 0° to about 60° C. for about 1 to about 70 hours.

Certain compounds of Formula (1.0) can be converted to other compounds of the Formula (1.0) using standard reaction conditions. For example, compounds of the formula (1.0) wherein $R^2$ and/or $R^3$ is —$CO_2H$, (i.e., —$C(O)OP^8$ and $R^8$ is H), can be prepared by ozonolysis of a compound (1.0) wherein $R^2$ and/or $R^3$ is $CH_2$=CH—, followed by oxidation of the resulting aldehyde to give other desired compounds (1.0).

Compounds (1.0) wherein $R^2$ and/or $R^3$ is —$C(O)OR^8$, where $R^8$ is other than H, can be prepared from compound (1.0) wherein $R^2$ and/or $R^3$ is —$CO_2H$ by treating with $SOCl_2$ or oxalyl chloride, then with an alcohol of the formula $R^8OH$, wherein $R^8$ is as defined above. Similarly, compounds of formula (1.0) wherein $R^2$ and/or $R^3$ is —$C(O)NR^8R^9$ can be prepared from a compound (1.0) wherein $R^2$ and/or $R^3$ is —$CO_2H$ via essentially the same method but substituting an amine of the formula $R^8R^9NH$ for the alcohol $R^8OH$. Alternatively, compounds of Formula (1.0) wherein $R^2$ and/or $R^3$ is —$C(O)NR^8R^9$ can be prepared by reacting a compound (1.0) wherein $R^2$ and/or $R^3$ is —$CO_2H$ with an amine $R^8R^9NH$ in the presence of a coupling agent, such as DCC or DEC.

In an analogous manner, compounds (1.0) wherein $R^2$ and/or $R^3$ is alkyl substituted by a group of the formula —$C(O)OR^8$ or —$C(O)NR^8R^9$ can be prepared via substantially the same procedures as described above to form compounds wherein $R^2$ and/or $R^3$ is —$CO_2H$, —$C(O)OR^8$ or —$C(O)NR^8R^9$, by replacing the compound (1.0) wherein $R^2$ and/or $R^3$ is $CH_2$=CH— with an appropriate alkenyl group, (i.e., a group of the formula —$(CH_2)p$—CH=$CH_2$, wherein p is 1, 2, 3, 4, etc.).

Compounds (1.0) wherein $R^2$ and/or $R^3$ contains a substituent of formula —$S(O)_tR^8$, wherein t=1 or 2, can be prepared by oxidation of an analogous compound of the formula (1.0) wherein $R^2$ and/or $R^3$ contains a substituent of formula $-S(O)_tR^8$, wherein t=0, using a suitable oxiding agent, such as a peracid, preferably MCPBA.

One skilled in the art will recognize that the above transformations may, in certain instances, such as where $R^1$ is a group of the formula

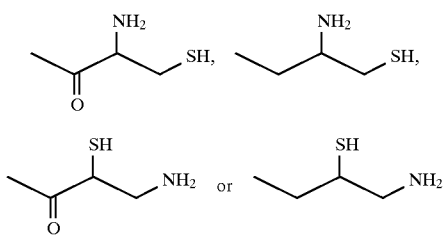

require that the oxidation be carried out prior to introduction of the $R^1$ group to formula (1.0).

Compounds (1.0) where the —Z group contains an N—O moiety, can be prepared by treatment of the carboxylic acid (8.0) containing a nitrogen atom (N) in the aromatic ring, with an oxidizing reagent, such as m-chloroperoxybenzoic acid or hydrogen peroxide and acetic acid. The subsequent carboxylic acid (8.0) containing the N—O moiety can be treated as described herein to give desired compound (1.0).

B. Process B for Preparing Piperazinyl Compounds

In alternative Process B, the piperazinyl compounds (1.0) of the present invention can be prepared according to the following Process B.

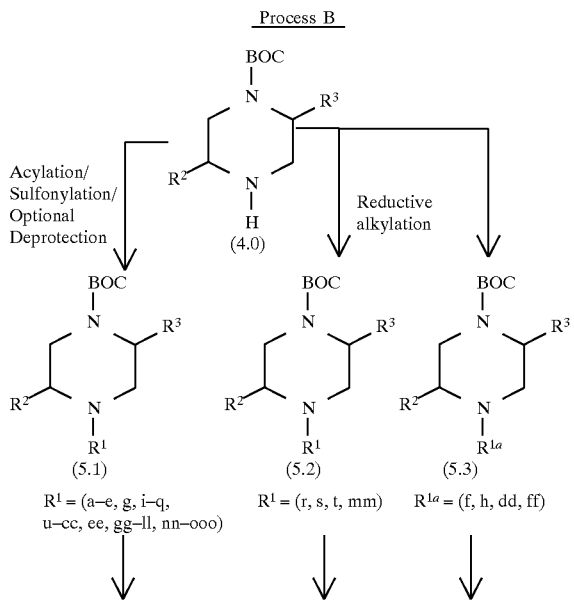

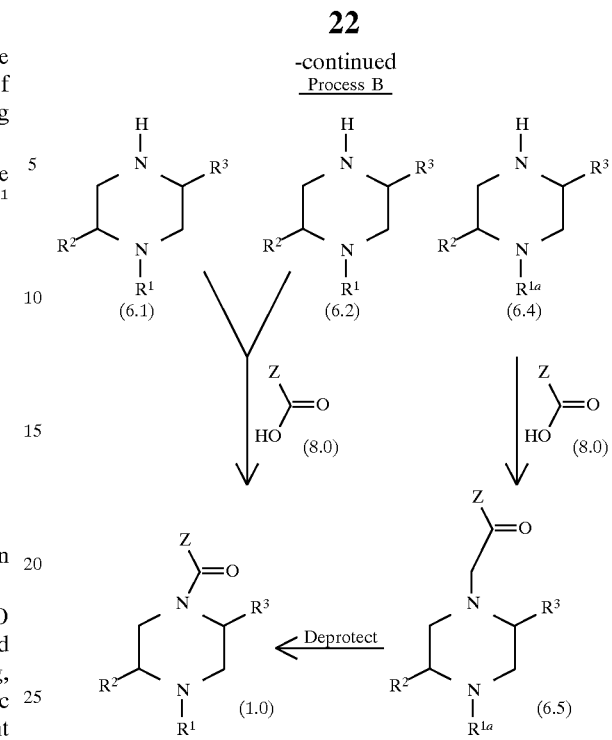

wherein Z, BOC, $R^1$=(a-ooo), $R^2$ and $R^3$ are as defined herein. It is also understood that groups $R^1$=(e, g, cc and ee) in compound (5.1) and groups $R^1$=(r, s, t, mm) in compound 5.2 and $R^1$=(f, h, dd and ff) in compound (5.3) are either N-protected as the BOC derivative or both N-protected as the BOC derivative and S-protected as the trityl (triphenylmethyl) derivative.

Process B, compound (4.0) can be either acylated or reductively alkylated (ie. reductively aminated) as described hereinbefore, to incorporate the $R^1$ group to give compounds (5.1), (5.2) and (5.3) respectively. Compounds (5.1), (5.2) and (5.3) can be deprotected with any suitable acid, such as trifluoracetic acid (TFA) or dioxane saturated with HCl gas, in a suitable solvent, such as methylene chloride ($CH_2Cl_2$) or dioxane to remove the BOC protecting group and yield compounds (6.1), (6.2) and (6.4), respectively. Reaction of compounds (6.1), (6.2) and (6.4) with carboxylic acid (8.0) under conditions and with reagents as described herein, gives the desired piperazinyl compounds (1.0) and (6.5) .Compound (6.5) is deprotected as described herein to give compound (1.0).

C. Piperidinyl Compounds and Starting Materials. The piperidinyl compounds of the present invention and starting materials thereof, can be prepared according to the following overall Process C.

23

Process C

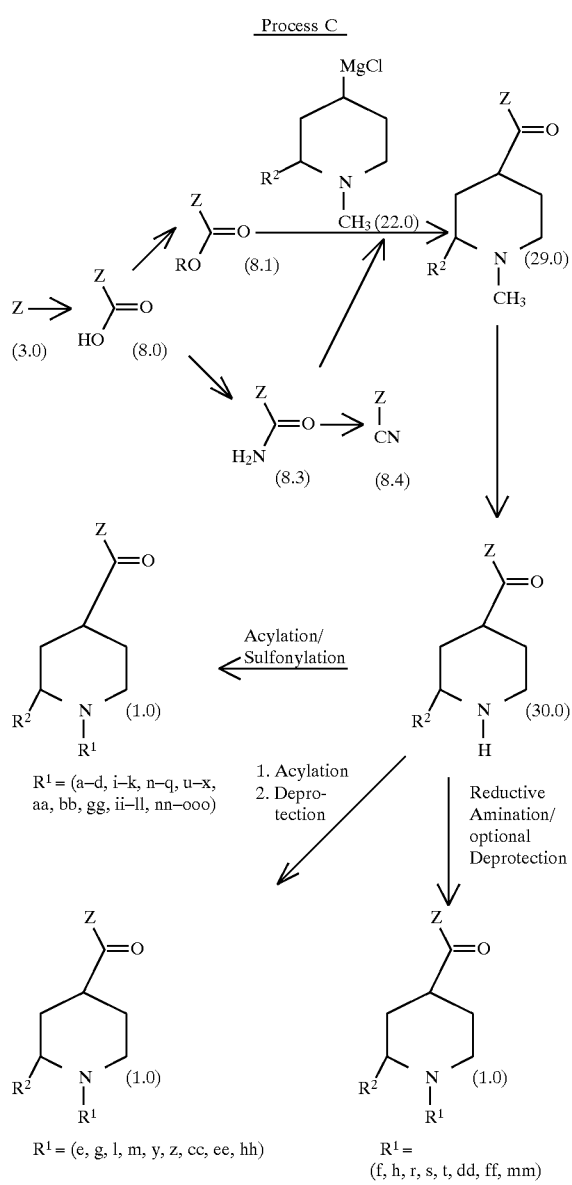

wherein Z, R, R¹=(a-ooo) and R² are as defined herein.

C1. Preparation of Piperidinyl Starting Materials.

The preparation of aromatic compounds (3.0) and their corresponding carboxylic acids (8.0) has been described in the section A1, for the preparation of the piperizinyl starting materials.

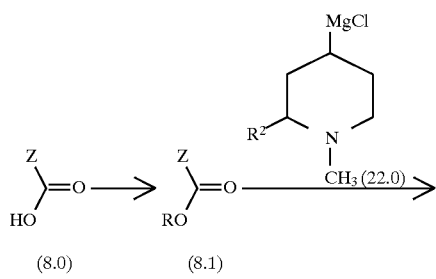

24

-continued

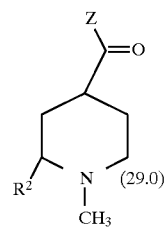

The carboxylic acids (8.0) can be converted to esters (8.1) by reacting the carboxylic acid with an alcohol such as methanol, in the presence of an acid such as sulfuric or hydrochloric acid to give ester (8.1). Ester (8.1) can be converted to the piperidyl ketone (29.0) by reaction of ester (8.1) with an organometallic reagent (22.0), such as as a Grignard reagent or an organolithium reagent.

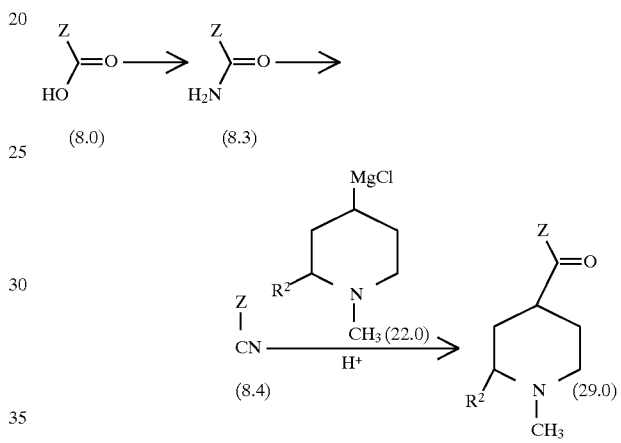

In an alternative reaction, the carboxylic acids (8.0) can be converted into amides (8.3) by treatment with ammonia and a coupling agent such as DCC or DEC. The amide (8.3) can then be dehydrated to nitrile (8.4) by treatment with a reagent such as phosphorous pentachloride ($P_2Cl_5$), thionyl chloride ($SOCl_2$) or acetic anhydride by methods well known to those skilled in the art, as taught in Ian Harrison and Shuyen Harrison, Compendium of Organic Synthetic Methods, John Wiley and Sons, New York, (1971) and Volume 2, (1974). The nitrile (8.4) can be converted to ketone (29.0) by treatment with an organometallic reagent, such a Grignard reagent or an organolithium reagent, followed by hydrolysis with acid to give protonated piperidyl ketone (29.0).

Compounds (1.0) wherein $X^1$ is CH, and $R^2$ is alkyl, alkenyl or alkynyl, or $R^2$ is alkyl, alkenyl or alkynyl substituted with substituents (a), (b), (c), (d), or (g) with the exception that substituents $R^8$ or $R^9$ cannot have a halogen, —OH, —C(O)$R^{13}$ or —SO$_2$$R^{13}$ substituent, can be made from compounds of the Formula 22.0:

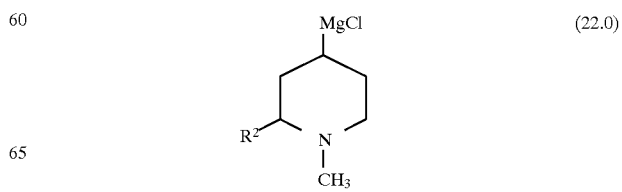

Compound (22.0) can be made according to the process:

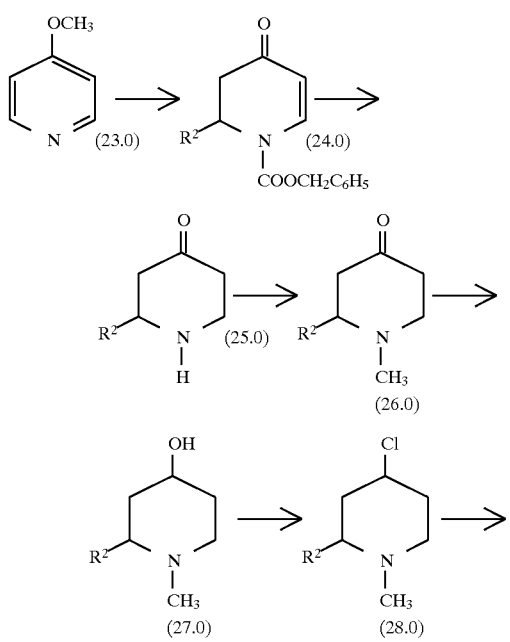

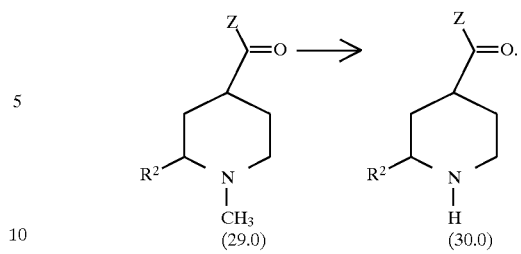

The substituted piperidines (22.0) may be prepared, as racemic mixtures, by essentially the same methods as described in D. L. Comins and J. D. Brown, Tetrahedron Letters, vol. 27 No. 38, pgs. 4549–4552, 1986. Thus, 4-methoxypyridine (23.0) may be converted using a variety of alkyl Grignard reagents (wherein $R^2$ is as illustrated below) and benzylchloroformate to the desired unsaturated ketopiperidines (24.0). Removal of the benzylcarbamoyl group with concomitant reduction of the double bond by catalytic hydrogenation yields the substituted ketopiperidines (25.0). Alternatively, the benzylcarbamoyl group can be removed with either base or acid followed by metal hydride reduction of the double bond to produce compound (25.0). Alkylation of the compound (25.0) with a suitable alkyl iodide such as methyl iodide in the presence of sodium hydride gives the n-alkylketopiperidines (26.0). Reduction of compound (26.0) with sodium borohydride affords the hydroxypiperidine (27.0). Compound (27.0) is reacted with a suitable chlorinating agent such as thionyl chloride to afford the 4-chloropiperidine(28.0) which may in turn be converted by reaction with magnesium into compound (22.0).

Compound (22.0) is reacted with the compound (8.1 or 8.4), described above, in a suitable solvent such as diethyl ether or THF. The reaction is conducted at room temperature (about 25° C.) to about 50° C. This reaction is then followed by aqueous acid hydrolysis to yield ketones (29.0):

The N-methyl group on the piperidine ring can be converted to a carboethoxy group ($-COOC_2H_5$) or a carbochloroethoxy group ($-COOCHClCH_3$) by reaction with excess ethyl chloroformate or 1-chloroethylchloroformate in dry toluene or dichloroethane containing triethylamine at a temperature of about 80° C. This procedure is similar to that described in U.S. Pat. Nos. 4,282,233 and 4,335,036. The carboethoxy group can be removed by either acid or base hydrolysis to give the compound (30.0). The carbochloroethoxy group can be removed by heating in methanol to give (30.0).

Compounds (30.0) are prepared as diasteromeric mixtures. Preferably, the diasteriomers are separated into single isomers by classical resolution methods or by chiral HPLC to yield:

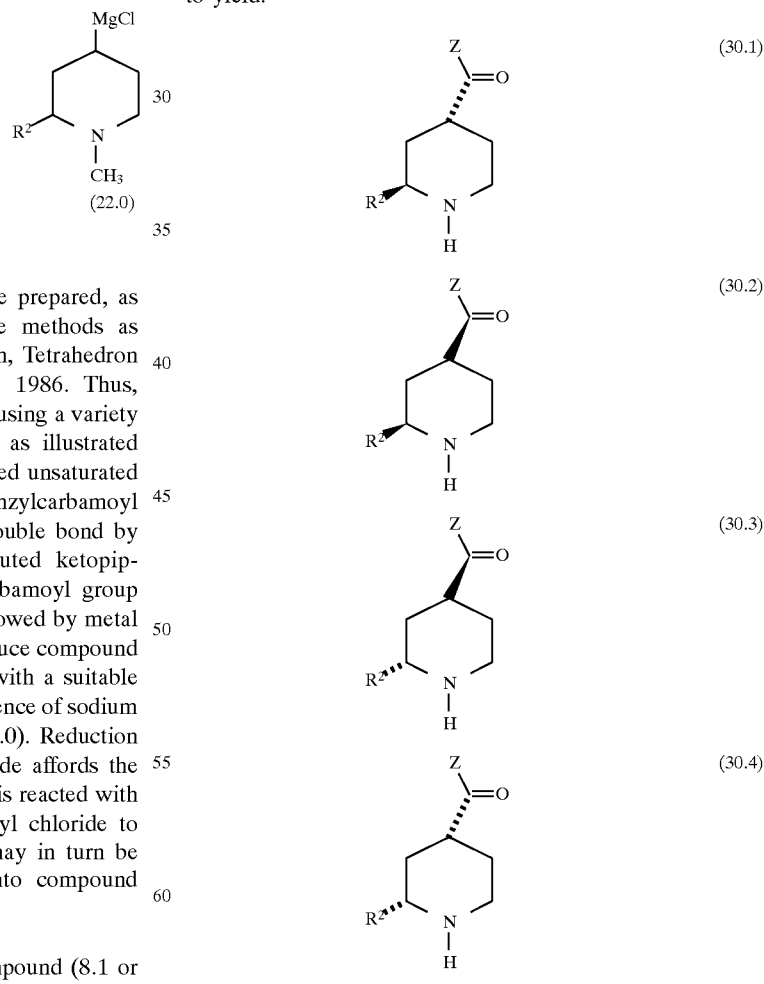

Compound (30.1), (30.2), (30.3) and (30.4) can be converted to the compound (1.0), wherein $X^1$ in (1.0) is CH, by acylation or reductive alkylation.

C2. Preparation of Piperidinyl Compounds.

The piperidinyl compounds (1.0) wherein $X^1$ is CH, can be prepared from the piperidinyl ketone (30.0), by using the acylation, acylation and deprotection or reductive alkylation/optional deprotection procedures described for Process A or B.

D. Process D for Preparing Piperazinyl Compounds

In an alternative embodiment, an encoded combinatorial library of compounds compounds (1.0) wherein $X^1$ is N and $R^2$ has a suitable functional group, can be prepared using combinatorial methods on a solid phase as described in WO94/08051, April 1994, whose preparative teachings are incorporated herein by reference and according to the following Process D.

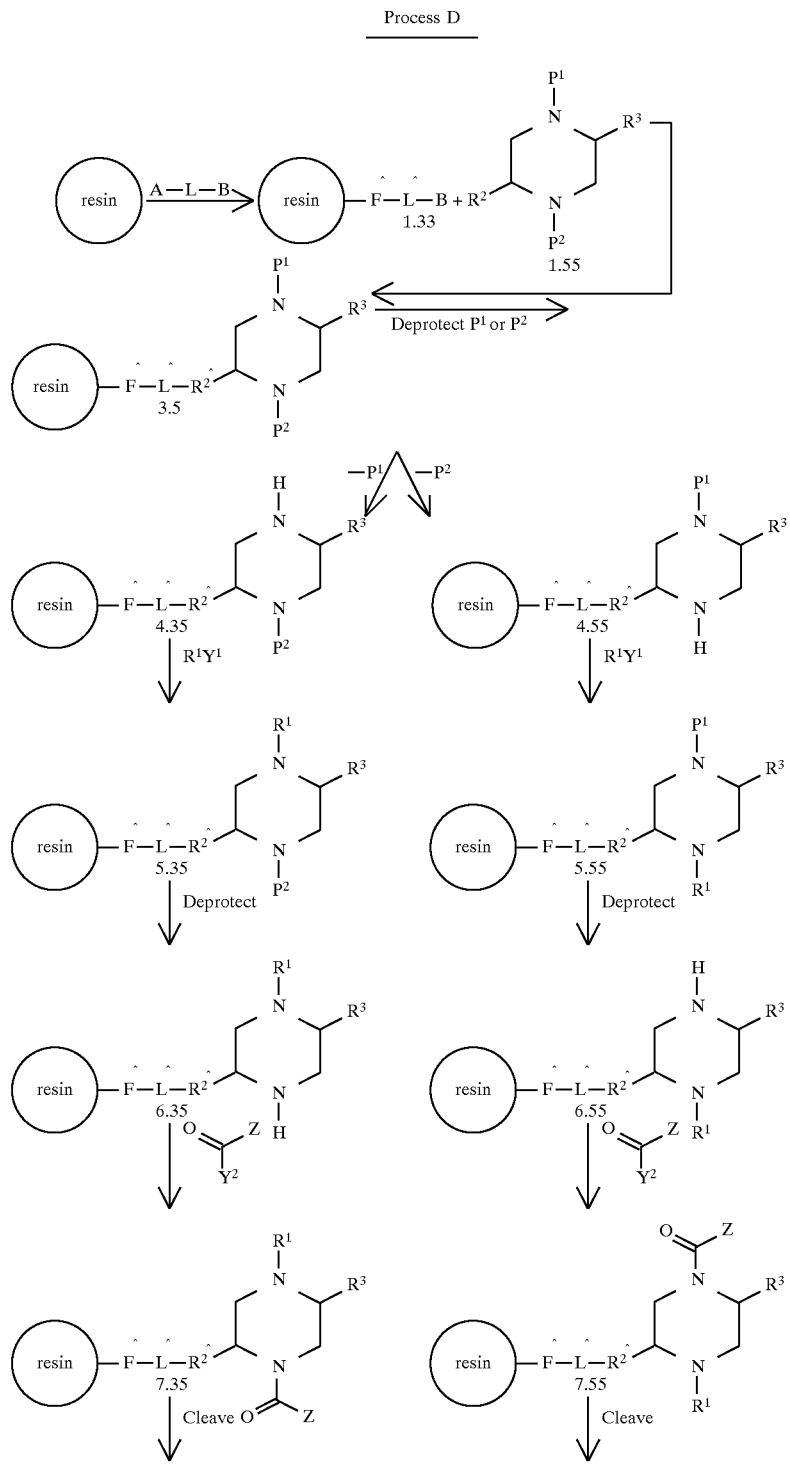

-continued
Process D

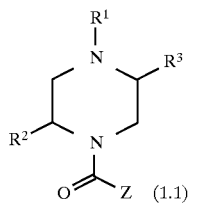 (1.1)  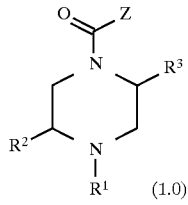 (1.0)

In Process D, a resin, e.g. (resin)—F, is selected which contains a functional group, (—F), which can couple, or form a covalent bond with a suitable linker (A—L—B). Suitable functional (—F) groups include primary and secondary amines, hydroxy, thiol, carboxylic acid, halide and the like. The linker can be any compound having (a) a complementary functional "A—" group (e.g. amine, hydroxy, thiol, carboxylic acid, halide and the like) which can couple, or form a covalent bond with (resin)—F, and (b) a functional "—B" group (e.g. hydroxy, primary or secondary amine, thiol, carboxylic acid and the like) capable of forming a covalent bond with a suitable functional group in either $R^2$ or $R^3$ of a substituted, N-protected piperazine (1.5), such as an amide or carboxylic acid group in $R^2$ or $R^3$, and (c) any organic or inorganic moiety L having bound to it functional groups A and B. Representative linkers include, but are not limited to 4-(bromomethyl)-3-nitrobenzoic acid and 4-(hydroxymethyl)phenol. The linker can be coupled to (resin)—F in a suitable solvent (e.g. DCM or methanol), optionally in the presence of a catalyst suitable for the particular coupling reaction.

Reagents and reaction conditions for protecting and deprotecting compounds is well known, as described, for example, in T. W. Greene and P. Wuts, Protective Groups in Organic Synthesis, 2nd Ed., Wiley Interscience, N.Y. 1991, 473 pages. In addition to having a suitable functional group in either its $R^2$ or $R^3$ group, piperazine 1.55 has protecting groups, $P^1$ and $P^2$ orthogonal to each other and to the linker. Suitable protecting groups include but are not limited to BOC, FMOC, CBZ, allyloxycarbonyl (ALLOC), benzyl, o-nitrophenyl and the like. The resin/linker 1 can be coupled to N-protected piperazine 1.55 in the presence of a suitable solvent, optionally in the presence of a catalyst suitable for the particular coupling reaction to give the coupled piperazine 3.5.

One of protecting groups $P^1$ or $P^2$ can be removed by treatment with a suitable deprotecting agent or process, including but not limited to TFA, piperidine, hydrogenolysis, photolysis and the like to give partially deprotected piperazine 4.35 or 4.55. Piperazine 4.35 or 4.55 can then be reacted with compound $R^1Y^1$ wherein $R^1$ is as defined before and $Y^1$ is a suitable leaving group, in a suitable solvent, optionally in the presence of a catalyst suitable for the particular reaction, to give partially protected piperazine 5.35 and 5.55. Compound 5.35 and 5.55 can be deprotected as described above to give deprotected compound 6.35 or 6.55. Compound 6.35 and 6.55 can be reacted with carbonyl compound $Z(CO)Y^2$ wherein Z is defined before and $Y^2$ is a suitable leaving group to give compound 7.35 or 7.55. The "^" in moieties such as $R^{2\wedge}$, $F^\wedge$ and $L^\wedge$ indicate that at least one functional group in that moiety is covalently bonded to another functional group.

Compound 1.0 can be prepared by cleaving the coupling between the linker and $R^{2\wedge}$ using a suitable reagent or process suitable for the particular bond coupling,.e.g. photolysis, acidolysis, hydrolysis and the like.

Compounds of the present invention and preparative starting materials thereof, are exemplified by the following examples, which should not be construed as limiting the scope of the disclosure. Alternative mechanistic pathways and analogous structures within the scope of the invention may be apparent to those skilled in the art, such as by the methods described in WO95/10516.

PREPARATIVE EXAMPLE 1

A. ETHYL 3-PYRIDYLACETIC ACID 1-N-OXIDE

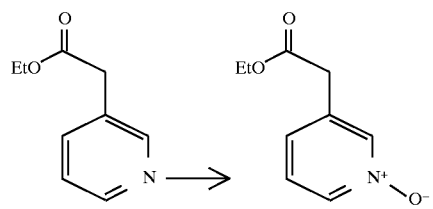

Ethyl 3-pyridylacetic acid (10grams) (60.6 mmoles) is dissolved in dry $CH_2Cl_2$ (120ml) and the solution is stirred at −18° C. for 30 minutes. MCPBA (31.34 grams) (181.6 mmoles) is added and the mixture is stirred at −18° C. for 1 hour and then at 25° C. for 87 hours. The reaction mixture is diluted with $CH_2Cl_2$ and washed with saturated aqueous sodium bicarbonate and then water. The $CH_2Cl_2$ is then dried (magnesium sulphate), filtered and evaporated to dryness. The residue was chromatographed on silica gel using 3% (10% concentrated ammonium hydroxide in methanol) —$CH_2Cl_2$ as the eluant to give the title compound (Yield: 8.45 grams, 77%, $MH^+$ 182).

B. 3-PYRIDYLACETIC ACID 1-N-OXIDE

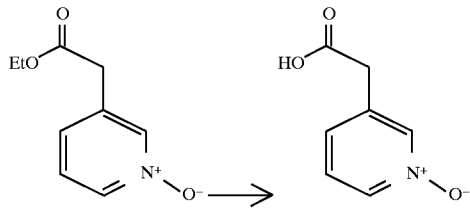

Ethyl 3-Pyridylacetic acid 1-N-oxide (0.2747 grams) (1.5 mmoles) is dissolved in ethanol (200 proof) (1.22 ml.) and a 1M solution of LiOH in water (3.64 ml.) (3.0 mmoles) is added and the mixture is stirred at 25° C. for 4 hours. 1N HCl (4.28 ml.) is added and the mixture is pumped down to dryness on a rotary evaporator to give the title compound (Yield: 0.2931 grams, 100%).

PREPARATIVE EXAMPLE 2

4-ETHOXYCARBONYLAMINOPYRIDINE

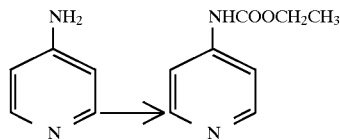

4-Aminopyridine (17.34 grams) (184.3) is dissolved in dry pyridine (217 ml.) and cooled to 0° C. over 30 minutes. Ethyl chloroformate (17.2 ml.) (180.7 mmoles) is added and the solution is stirred at 0° C. for 1 hour and then at 25° C. for 40 hours. The mixture is diluted with $CH_2Cl_2$ and washed with saturated aqueous $NaHCO_3$ and water. The $CH_2Cl_2$ is dried ($MgSO_4$), filtered and evaporated to dryness. The residue is chromatographed on silica gel using 2%(10% saturated $NH_4OH$ in MeOH)—$CH_2Cl_2$ to give the title compound (Yield: 10 grams, 33%, $M^+$ 166).

By using essentially the same procedure, with the exception that

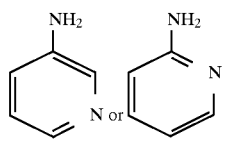

is used instead of 4-aminopyridine, the compound

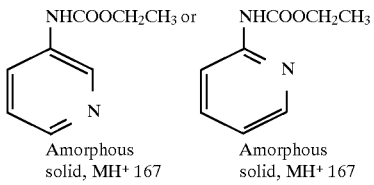

is obtained, respectively.

PREPARATIVE EXAMPLE 3

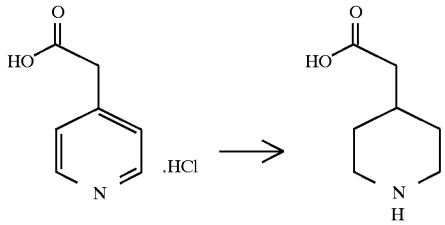

4-Pyridylacetic acid hydrochloride (7 grams) (40.4 mmoles) is hydrogenated in water (100 ml) using 10% Pd-C at 40 psi at 25° C. for 24 hours. The catalyst is filtered off and washed with water. The aqueous solution is shaken with BioRad AG1X8 resin ($OH^-$ form) (23 ml bed) and after 5 minutes the resin is filtered off and washed with water. The aqueous solution is evaporated to give the title compound (Yield: 5.2 grams, 90%, $MH^+$ 144).

B. 1-N-ACETYL-4-PIPERIDINYLACETIC ACID

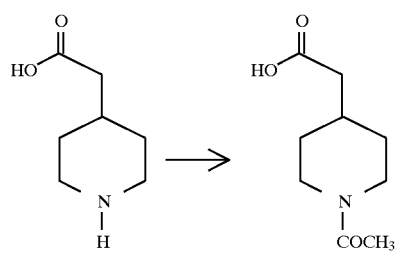

4-Piperidinylacetic acid (5 grams) (35.0 mmoles) is reacted with acetic anhydride (10.7 grams) (105.0 mmoles) in MeOH (100 ml.) and the mixture is stirred at 25° C. for 24 hours. The mixture is evaporated to dryness and the residue is azeotroped with toluene to give the title compound (Yield: 6.4 grams, 99%, $MH^+$ 185).

C. 1-N-METHYL-4-PIPERIDINYLACETIC ACID

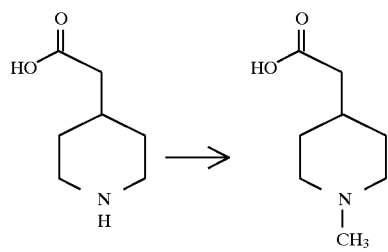

4-Piperidinylacetic acid (4 grams) (28.0 mmoles) from Preparative Example 3A is dissolved in water (50 ml) and 37% formalin (2.72 ml) (33.6 mmoles) is added. The mixture is hydrogenated over 10% Pd-C at 55psi at 25° C. for 68 hours. The catalyst is filtered off and washed with water. The combined filtrates are evaporated to dryness to give the title compound ( $MH^+$158).

D. 1-N-tert-BUTOXYCARBONYLPIPERIDINYL-4-ACETIC ACID

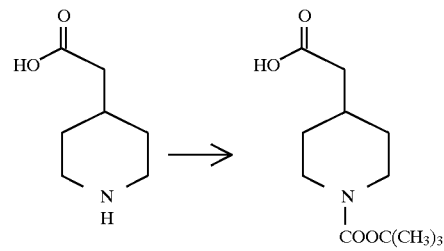

4-Piperidinylacetic acid (41.24 grams) (288.4 mmoles) from Preparative Example 3A is dissolved in THF-water (1:1) (400 ml) and di-tert-butyldicarbonate (69.14 grams) (317.3 mmoles) and NaOH (11.52 grams) (288.4 mmoles) are added. The mixture is stirred at 25° C. for 72 hours. The solution is then eluted through a bed of washed BioRad 50WX4 (RSO3H resin) (150 ml bed) and the resin is eluted with a 1:1 mixture of THF and water. The eluate is evaporated to dryness to give the title compound (Yield: 53.0 grams, 76%).

PREPARATIVE EXAMPLE 4
A. 3-PIPERIDINYLACETIC ACID

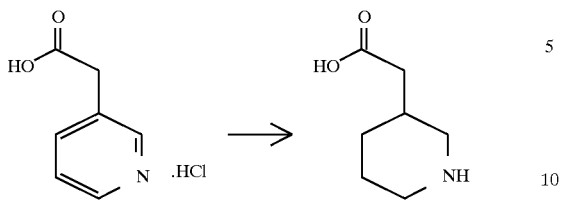

3-Pyridylacetic acid hydrochloride (13 grams) (74.9 mmoles) is hydrogenated as described in Preparative Example 3A to give a mixture of unreacted 3-pyridylacetic acid and the title compound (76:24) (8.63 grams, MH$^+$ 144).

B. 1-N-ACETYL-3-PIPERIDINYLACETIC ACID

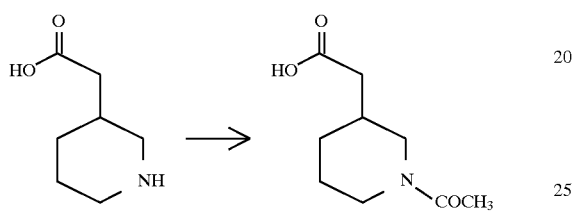

The mixture of compounds from Preparative Example 4A (8.56 grams) are reacted with acetic anhydride (8.56 grams) as described in Preparative Example 3A and the crude mixture of products is diluted in methanol (60 ml) and passed over a bed of BioRad AG50WX4 resin (RSO$_3$H) and the latter is eluted with methanol. The eluates are evaporated to dryness to give the title compound (Yield: 1.23 grams, MH$^+$ 186).

C. 1-N-METHYL-3-PIPERIDINYLACETIC ACID

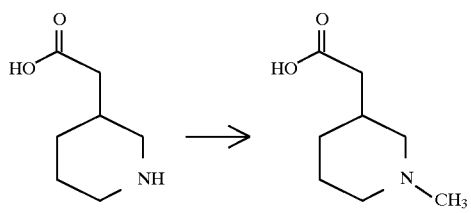

The mixture of compounds from Preparative Example 4A (4 grams) and 37% formalin (2.72 ml.) are hydrogenated as described in Preparative Example 3C to give the title compound (MH$^+$ 158).

PREPARATIVE EXAMPLE 5
3-PYRIDYLISOCYANATE, HYDROCHLORIDE

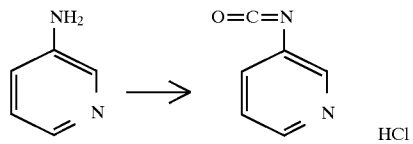

A 1.93M solution of phosgene in toluene (20%) (584 mL) is diluted with dry CH$_2$Cl$_2$ (1 L) and the mixture is stirred at 0° C. under nitrogen atmosphere. A solution of 3-aminopyridine (21.1 grams) and dry pyridine (19 mL) dissolved in dry CH$_2$Cl$_2$ (600 mL) is added dropwise to the stirred solution at 0° C. over a period of 5.5 hours. The mixture is stirred at 0°–25° C. for an additional 48 hours. A stream of nitrogen is passed through the solution to remove most of the phosgene and the solution is then evaporated until almost all of the solvent is removed to give the title compound which is then taken up in dry pyridine (850 mL) to give a stock solution of the title compound.

PREPARATIVE EXAMPLE 6

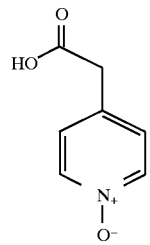

Step A:

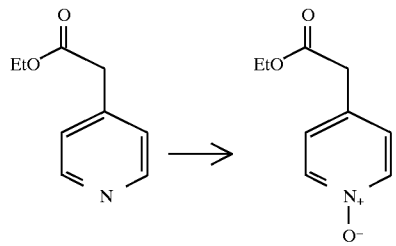

Combine 10 g (60.5 mmol) of ethyl 4-pyridylacetate and 120 mL of dry CH$_2$Cl$_2$ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with CH$_2$Cl$_2$ and wash with saturated NaHCO$_3$ (aqueous) and then water. Dry over MgSO$_4$, concentrate in vacuo to a residue, and chromatograph (silica gel, 2%–5.5% (10% NH$_4$OH in MeOH)/CH$_2$Cl$_2$)to give 8.12 g of the product compound (Et represents —C$_2$H$_5$ in the formula). Mass Spec.: MH$^+$= 182.15

Step B:

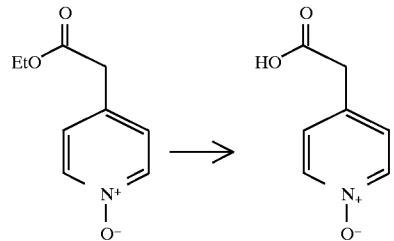

Combine 3.5 9 (19.3 mmol) of the product of Step A, 17.5 mL of ethanol and 96.6 mL of 10% NAOH (aqueous) and heat the mixture at 67° C. for 2 hours. Add 2N HCl (aqueous) to adjust to pH=2.37 and concentrate in vacuo to a residue. Add 200 mL of dry ethanol, filter through Celite® and wash the filter cake with dry EtOH (2×50 ml). Concentrate the combined filtrates in vacuo to give 2.43 g of the title compound.

PREPARATIVE EXAMPLE 7

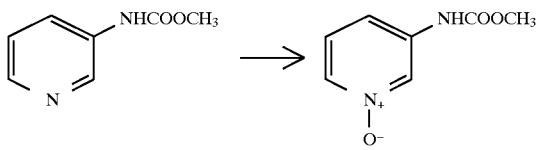

Combine 10 g (65.7 mmol) of 3-methoxycarbonylaminopyridine and 150 mL of $CH_2Cl_2$, cool to 0° C. and slowly add (dropwise) a solution of 13.61 g (78.84 mmol) of MCPBA in 120 mL of $CH_2Cl_2$ at 0° C. over a period of 1 hour. Stir the mixture at 25° C. for 5 days, then wash with saturated $NaHCO_3$ (aqueous), then water and dry over $MgSO_4$. Concentrate in vacuo to a residue and chromatograph (silica gel, 2%–5% (10% $NH_4OH$ in MeOH) /$CH_2Cl_2$) to give the product compound. Mass Spec.: $MH^+$= 169

PREPARATIVE EXAMPLE 8

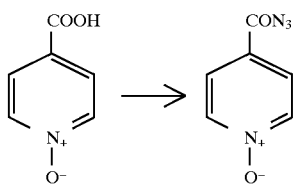

Combine 5 9 (36.0 mmol) of isonicotinic acid 1-N-oxide and 150 mL of anhydrous DMF, add 5.5 mL (39.6 mmol) of triethylamine and stir at 0° C. for 0.5 hours. Slowly add (dropwise) 8.5 mL (39.6 mmol) of diphenyl-phosphoryl azide at 0° C. over 10 minutes, stir at 0° C. for 1 hour and then at 25° C. for 24 hours (as generally described in Pavia, et al., *Journal of Medicinal Chemistry*, 33, 854–861 (1990). Concentrate in vacuo to a residue and chromatograph (silica gel, 0.5%–1% MeOH/$CH_2Cl_2$) to give 5.9 g of the product compound.

Using nicotinic acid 1-N-oxide and substantially the same procedure as described for Preparative Example 8 the following compound is prepared:

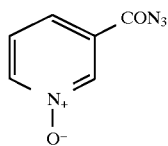

PREPARATIVE EXAMPLE 9
Step A:

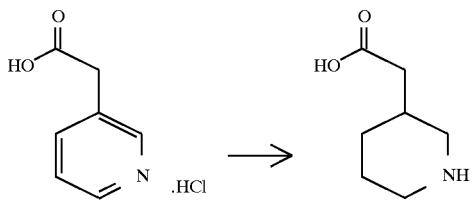

Hydrogenate 25 g (144 mmol) of 3-pyridylacetic acid hydrochloride for 144 hours using the procedure described in Preparative Example 3A to give 20 g of the product compound. Mass Spec.: $MH^+$=144.

Step B:

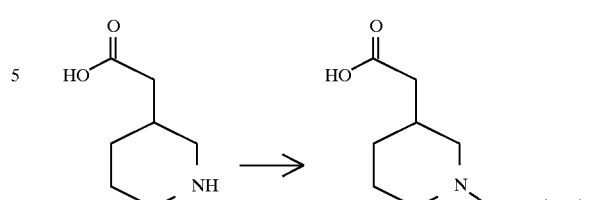

React 12 g (83.8 mmol) of the product of Step B for 148 hours using the procedure described in Preparative Example 3D, to give 17.5 g of the product compound. Mass Spec.: $MH^+$=244.25

PREPARATIVE EXAMPLE 10

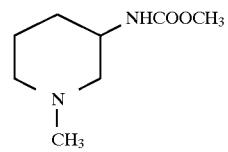

Combine 25 g (164.4 mmol) of methyl 3-pyridylcarbamate and 163.3 mL of 1N HCl (aqueous), stir until all of the solid dissolves, then hydrogenate over 10% Pd/C at 25° C. at 55 psi for 220 hours. Filter, wash the solids with water and treat the combined filtrates with 150 mL of BioRad AG1X8 ion exchange resin ($OH^-$). Filter, wash the resin with water and concentrate the filtrate to a volume of 100 mL. Add 16.43 mL (197.3 mmol) of 37% formalin and hydrogenate over 10% Pd/C at 25° C. at 55 psi for 89 hours. Filter, wash the solids with water and concentrate in vacuo to give 24.3 g of the title compound. Mass Spec.: $MH^+$= 173.2.

PREPARATIVE EXAMPLE 11

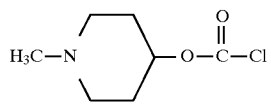

Combine 10 mL of dry $CH_2Cl_2$ and 914.6 mL (28.1 mmol) of a 1.93M solution of phosgene in toluene, cool to 0° C. and slowly add (dropwise) a solution of 0.6484 g (5.62 mmol) of 4-hydroxy-1-N-methylpiperidine, 1.214 mL (15 mmol) of pyridine and 10 mL of dry $CH_2Cl_2$ over 10 minutes, then stir at 0° to 25° C. for 2 hours. Purge excess phosgene with $N_2$ then concentrate in vacuo to give the title compound.

EXAMPLE 1

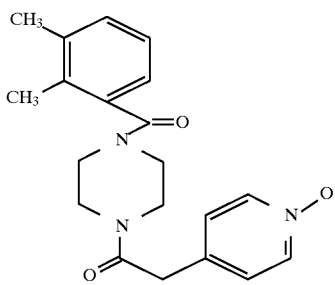

Step A:

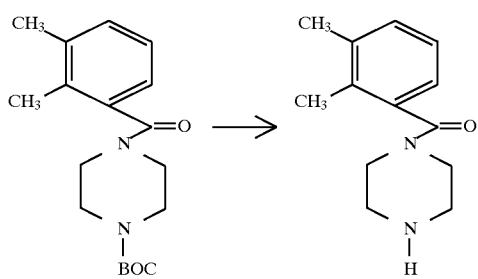

Dissolve 1-tert-butoxycarbonyl-4-(2,3-dimethylbenzoyl)-piperazine (described in WO 95/00497, p 45, Example 1) in dioxane saturated with HCl gas. After about one hour concentrate in vacuo and use the resulting HCl salt without purification.

Step B:

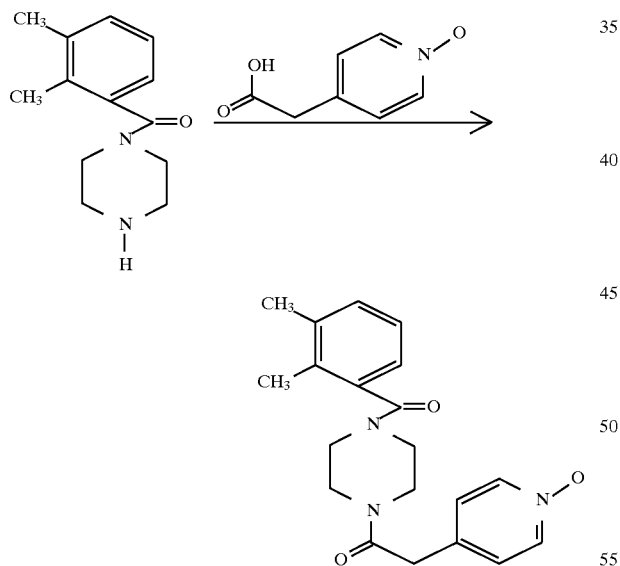

Dissolve the product of Step A in N,N-dimethyl formamide containing one equivalent of 1-hydroxybenzotriazole, (HOBT) one equivalent of 1-(3-dimethylaminopropyl)-3-ethylcarbodimide hydrochloride (DEC), one equivalent of 4-pyridylacetic acid-1-N-oxide and one equivalent of N-methylmorpholine. When reaction is complete, about 4 hours, the reaction is poured into water and extracted with ethyl acetate. The organic layer is dried over magnesium sulfate, filtered and concentrated in vacuo. The residue is chromotographed on silica gel using ethyl acetate-hexane to give the title compound.

EXAMPLE 2

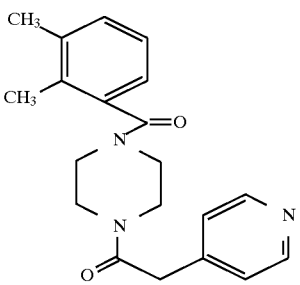

Perform the reaction of Example 1, Step B except use 4-pyridinylacetic acid instead of 4-pyridinylacetic acid-1-N-oxide to obtain the product.

EXAMPLE 3

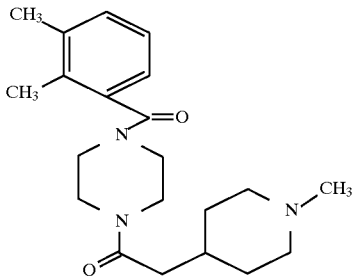

Perform the reaction of Example of 1, Step B except use N-methyl-4-piperidinylacetic acid (Preprative Example 3. Step C) instead of 4-pyridinylacetic acid-1-N-oxide to obtain the product.

EXAMPLE 4

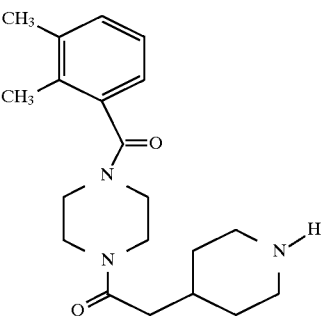

Step A:

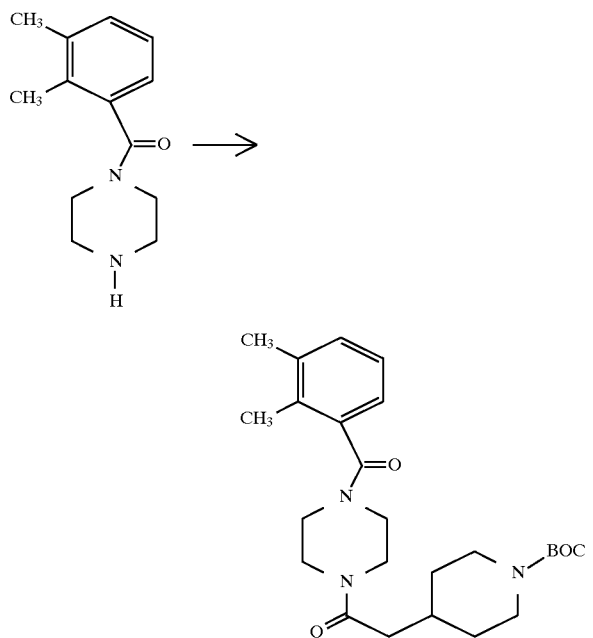

Perform the reaction of Example 1, Step B except use N-tert-butoxycarbonyl-4-piperidinylacetic acid (Preparative Example 3, Step D) instead of 4-pyridinylacetic acid-1-N-oxide to obtain the product.

Step B:

Dissolve the product of Step A in dioxane saturated with HCl gas and and allow to stir until complete, about 4 hours. Concentrate under vacuo. Partition between aqueous sodium bicarbonate solution and ethyl acetate. Dry the organic layer over magnesium sulfate, filter and concentrate in vacuo to give the title compound.

EXAMPLE 5

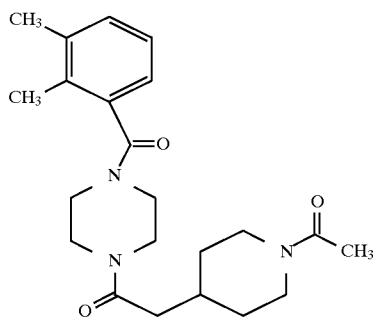

Dissolve the product of Example 4, Step B in pyridine and add 0.5 equivalent of acetic anhydride. Stir until complete, about 8 hours. Concentrate under vacuo. Dissolve in ethyl acetate, wash with brine, dry organic layer over magnesium sulfate, filter and concentrate in vacuo. Chromatograph on silica gel using ethyl acetate-hexane to give the title product.

EXAMPLE 6

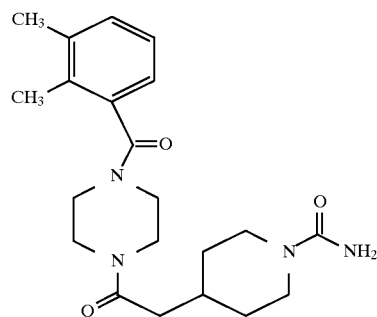

Dissolve the product of Example 4, Step B in methylene chloride and add excess trimethylsilylisocyanate. Stir under nitrogen for 18 hours. Wash with aqueous sodium bicarbonate solution. Dry the organic layer over magnesium sulfate, filter and concentrate in vacuo. Chromatograph the residue on silica gel using methanol-methylene chloride to give the product.

EXAMPLE 7

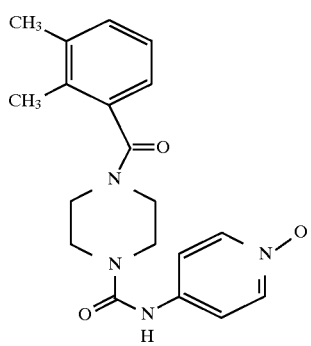

Dissolve the product of Preparative Example 8 in toluene and reflux for 2 hours. Cool to 25° C. and add one equivalent of the product of Example 1, Step A and allow to stand for 18 hours. Concentrate and chromatograph on silica gel using chloroform-methanol to give the product.

EXAMPLE 8

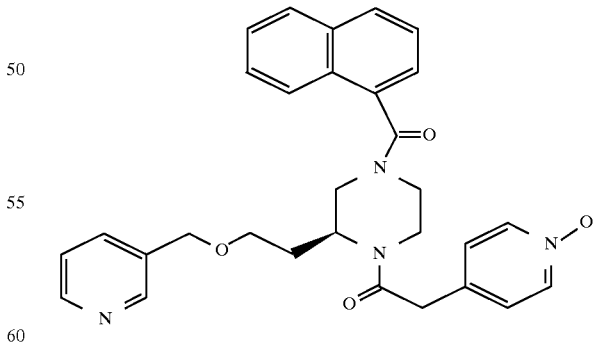

Dissolve 1-tert-butoxycarbonyl-(2(S)-2-(3-pyridyl-methoxyethyl)-4-(1-naphthoyl)piperazine (preparation described in WO 95/00497, Example 14) in dioxane saturated with HCl gas and allowed to stand until reaction is complete. Concentrate in vacuo and then react as described in Example 1, Step B to yield the product.

EXAMPLE 9

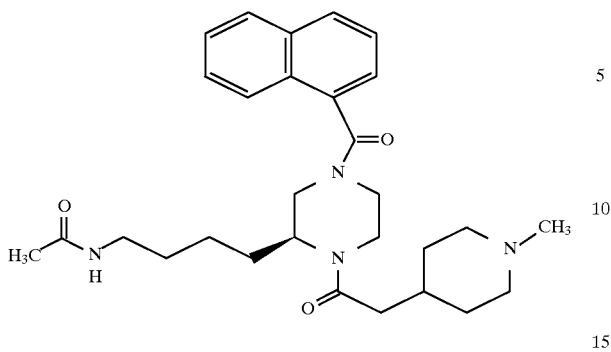

React 2(S)-4-acetamidobutyl)-4-(1-napthyl)- piperazine (preparation described in WO 95/00497, Example 27, Step G) with N-methyl-4-piperidinyl acetic acid (Preparative Example 4, Step C) by the process described in Example 3 to give the product.

EXAMPLE 10

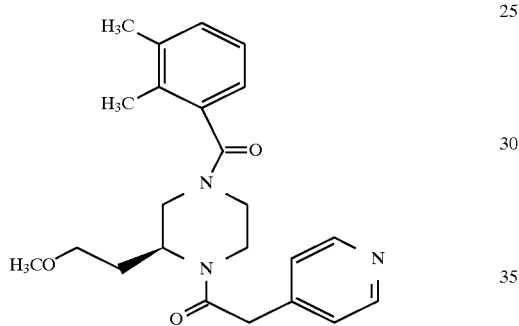

React 1-tert-butoxycarbonyl-4-(2,3-dimethylbenzoyl)-2 (S)-(2-methoxyethyl)-piperazine (preparation described in WO 95/00497, Example 7, Step E) with 4-pyridylacetic acid using the process described in Example 2 to give the product.

EXAMPLE 11

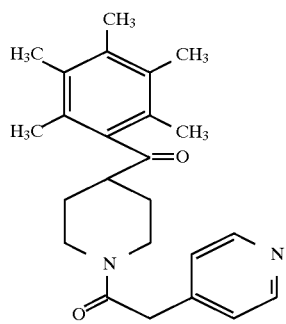

React 4-(pentamethylbenzoyl)-piperidine with 4-pyridylacetic acid by the process described in Example 2 and purify the crude product by silica gel chromatography using methanol-methylene chloride-amonia to give the product as a white solid, $M^+=379$.

EXAMPLE 12

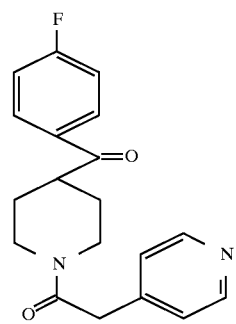

React 4-(4-fluorobenzoyl)-piperidine with 4-pyridylacetic acid by the process described in Example 2 to give the product as a white solid, $M^+=327$.

EXAMPLE 13

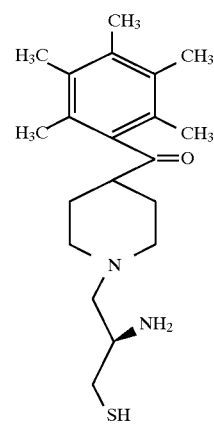

Step A:

Dissolve one equivalent of 4-(pentamethylbenzoyl)-piperidine in N,N-dimethyl formamide containing one equivalent of sodium triacetoxyborohydride and crushed molecular sieves. Cool this solution to 0° C. and add dropwise, a solution of 1 equivalent of 2(R)-tert-butoxycarbonylamino-3-triphenylmethylthiopropanal (preparation described in WO 95/00497, Example 1, Step C, and by O. P. Goel, et al. Organic Synthesis (1988), 67, 69–75) in N,N-dimethylformamide. Allow reaction to warm to 20° C. and stir under nitrogen for 2 hours. Concentrate in vacuo and partition the residue between ethyl acetate and saturated sodium bicarbonate solution. Dry the organic layer over magnesium sulfate, filter and concentrate in vacuo.

Step B:

Dissolve the product from Step A in methylene chloride and add five equivalents of triethylsilane. To this solution add trifluoroacetic (10 equivalents) and stir the reaction at 20° C. for 30 min. Concentrate in vacuo and partition between water and hexane. Chromatograph the water layer on a C18 HPLC column using acetonitrile water and 0.1% trifluoroacetic acid. The combined fractions are evaporated, dissolved in water and passed through a Biorad AG 3×4 (Cl⁻) ion exchange column to give the product as a hydrochloride salt.

EXAMPLE 14

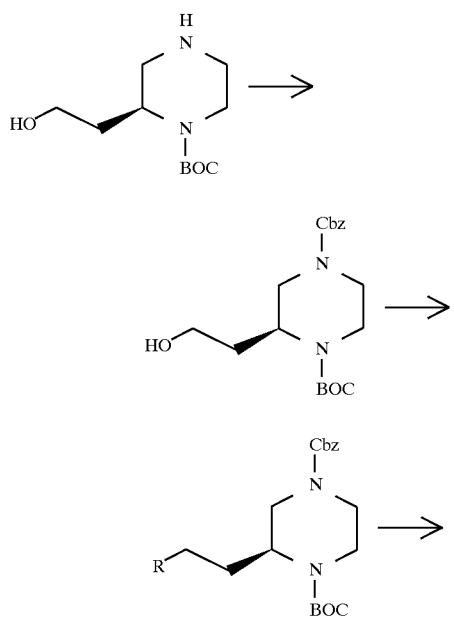

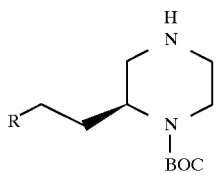

The title compound from Example 13A (WO 95/00497) is reacted with benzyloxycarbonyl chloride under standard conditions known to one skilled in the art, to give the N—Cbz protected alcohol shown above. After purification in the usual way the latter may be reacted with a variety of reagents shown in Column 1 of Table 1 to give the corresponding N—Cbz protected intermediates where R is as defined in Column 2 of Table 1 After purification in the usual way the latter may be deprotected using mild catalytic hydrogenation procedures known in the art, to give after suitable purification, the final desired intermediates shown in Column 2 of Table 1.

TABLE 1

| Column 1 | Coulmn 2 |
|---|---|
| 3-(chloromethyl)pyridine and NaH | 3-(pyridylmethoxy)— <br> Prepared as described in Example 14A (WO 95/00497) <br> Example 6. |
| $C_6H_5SSC_6H_5$ + (n-Bu)$_3$P | R = phenyl-$SO_2$— <br> Prepared as described in Example 20B and 20C (WO 95/00497) <br> Example 7. |
| (i) vinyl ethyl ether + Hg(OAc)$_2$ + CH$_3$COOH <br> (ii) CH$_2$I$_2$ + Et$_2$Zn | R = cyclopropyl-O— <br> Prepared as decribed in Examples 26A and 26B (WO 95/00497) <br> Example 8 |
| (i) EtOCON=NCOOEt + (C$_6$H$_5$)$_3$P + CH$_3$COSH <br> (ii) NH$_3$ + CH$_3$OH <br> + cyclopropyl-CH$_2$Br <br> (iii) Mg monoperphthalic acid + CH$_3$OH | R = cyclopropyl-CH$_2$SO$_2$— <br> Prepared as described in Examples 29A, 29B and 29C (WO 95/00497) <br> Example 9 |

TABLE 1-continued

| Column 1 | Coulmn 2 |
|---|---|
| n-$C_3H_7$I + NaH | n-$C_3H_7$O—<br>Prepared as described in Example 13C<br>(WO 95/004987)<br>Example 10 |

EXAMPLE 15

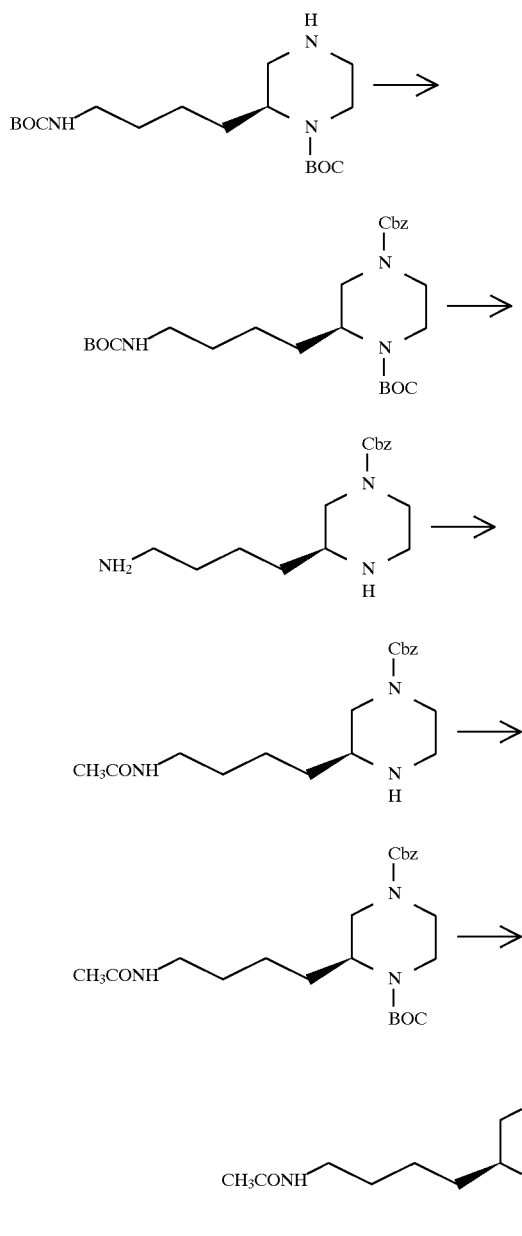

The title compound from Example 27D (WO 95/00497) is converted by the scheme shown above using standard procedures known to one skilled in the art into 1-tert-butoxycarbonyl-2(S)-(4-acetylaminobutyl)piperazine.

EXAMPLE 16

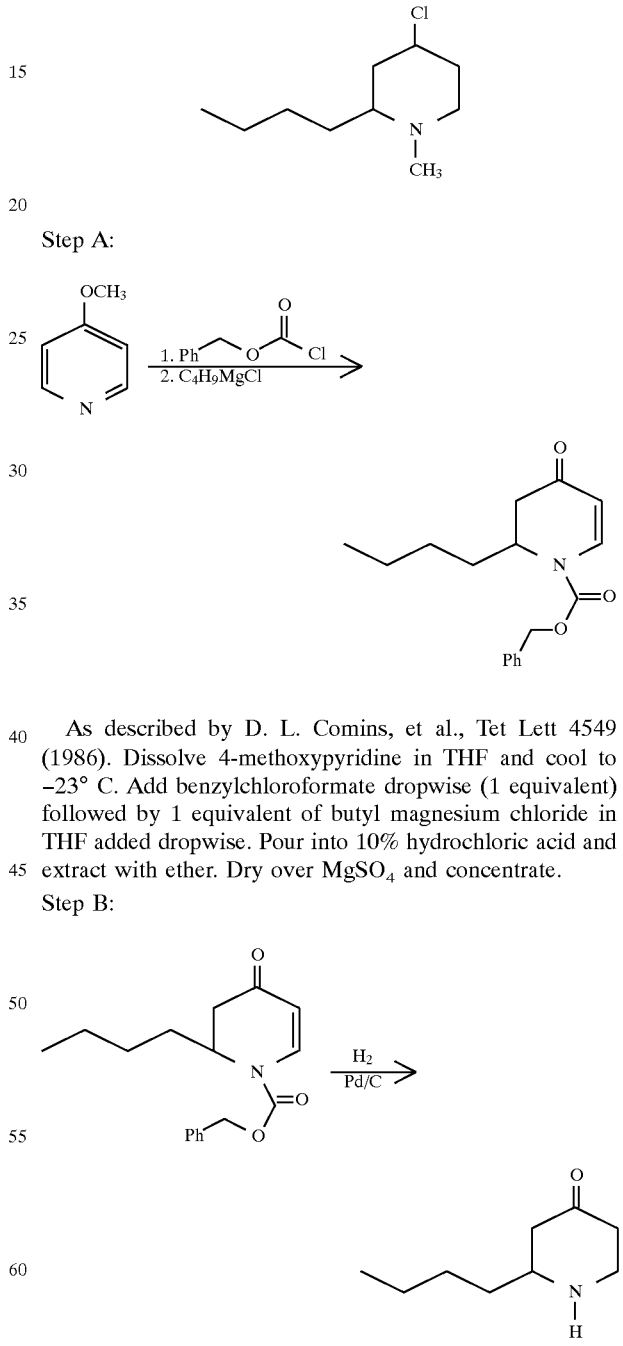

Step A:

As described by D. L. Comins, et al., Tet Lett 4549 (1986). Dissolve 4-methoxypyridine in THF and cool to −23° C. Add benzylchloroformate dropwise (1 equivalent) followed by 1 equivalent of butyl magnesium chloride in THF added dropwise. Pour into 10% hydrochloric acid and extract with ether. Dry over $MgSO_4$ and concentrate.

Step B:

Dissolve the product of Step A in ethanol containing 10% palladium on carbon and hydrogenate at 60 psi. Filter and concentrate in vacuo to obtain the product.

Step C:

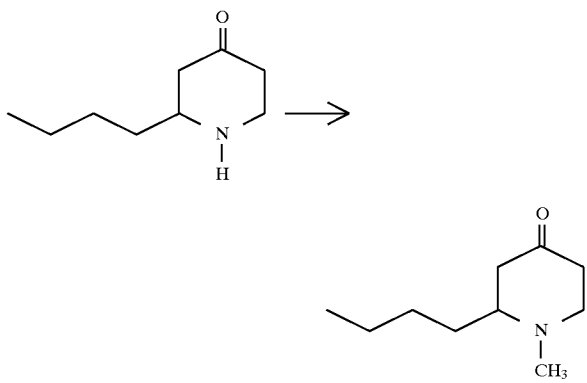

Dissolve the product of Step B in tetrahydrofuran, cool to 0° C. under nitrogen and add one equivalent of sodium hydride. After stirring for 15 min., one equivalent of methyl iodide is added. Stir reaction for 15 min., concentrate under vacuo and chromatograph on silica gel using methanol-methylene chloride.

Step D:

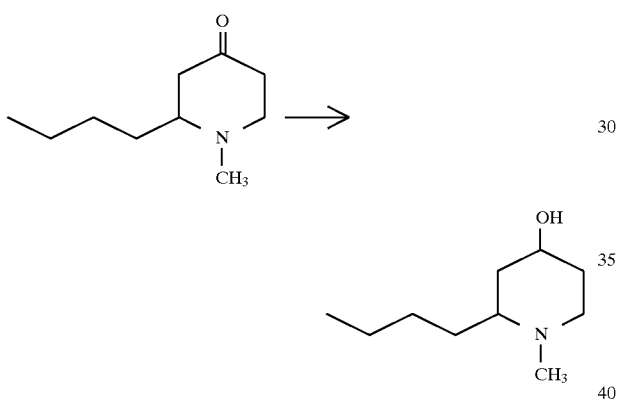

Dissolve the product of Step C in ethanol and add an excess of sodium borohydride. Concentrate in vacuo. Partition between water and ethyl acetate. Dry the organic layer over magnesium sulfate, filter and concentrate in vacuo.

Step E:

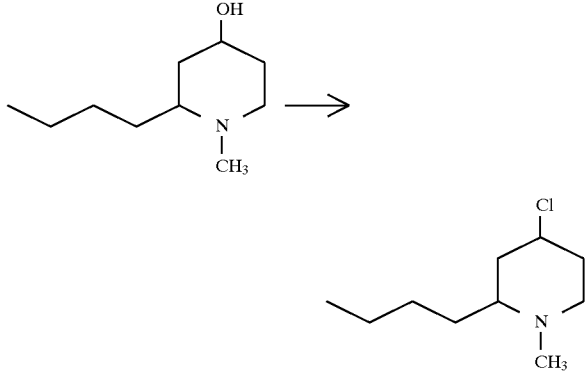

Dissolve the product of Step D in pyridine containing an excess of thionyl chloride. Stir for 18 hours and concentrate in vacuo. Partition between ethyl acetate and aqueous sodium bicarbonate. Dry the organic layer over magnesium sulfate, filter and concentrate in vacuo to obtain the product.

EXAMPLE 17

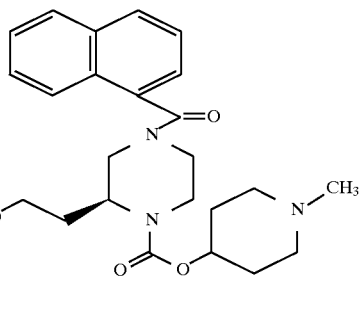

Dissolve 2(S)-2-(3-pyridyl-methoxyethyl)-4-(1-naphtholyl)piperazine (preparation described in WO 95/00497, Example 14, Step B) in methylene chloride containing one equivalent of triethylamine and cool to 0° C. under nitrogen. Add one equivalent of the product of Preparative Example 11 and allow the reaction to warm to room temperature. Stir at 25° C. until reaction is complete, about 10 hours. Concentrate in vacuo and chromatograph on silica gel using chloroform-methanol-ammonia to give the product.

EXAMPLE 18

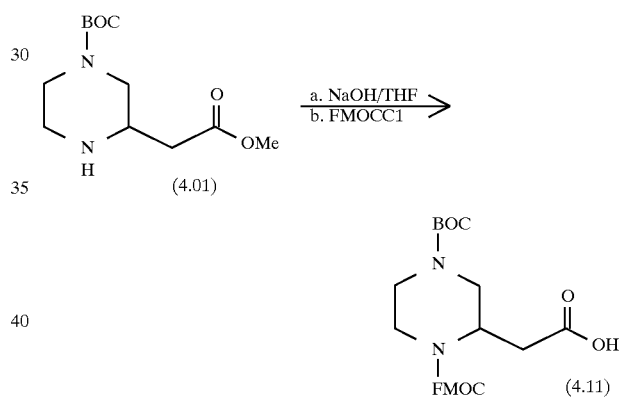

To the solution of above methyl 4-N-BOC-2-piperazine acetate (4.0) (5.2 g, 20 mmol) in THF (60 mL) is added 1N NaOH (60 mL). The reaction mixtures is stirred at room temperature for 6 hours, cooled to 0° C. and acidified to pH=9–10 by 10% HCl followed by the addition of FMOC—Cl (5.2 g, 20 mmole). The pH of the reaction mixture is kept at 9–10 by adding 1N NaOH. After room temperature for 6 hours, reaction mixture is acidified by 10% HCl to pH=1 and extracted with ethyl acetate twice. The combined organic layers are washed with brine, dried over MgSO$_4$ and concentrated to give 4-N-BOC-1-N-FMOC-2-piperazine acetic acid (4.1) (8.56 g, 89%) as a white foam.

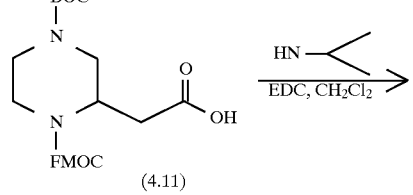

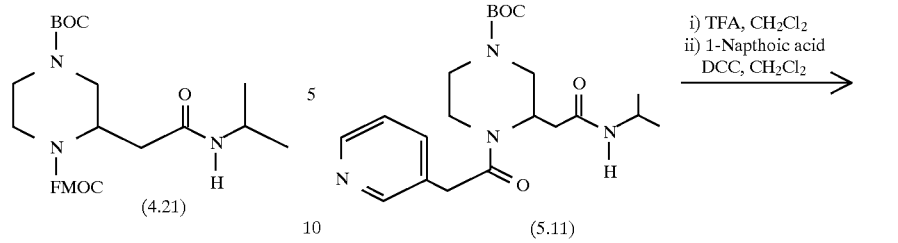

To the above 4-N-BOC-1-N-FMOC-2-piperazine acetic acid (4.1) (460 mg, 1 mmol) in 5 mL $CH_2C_{l2}$ is added EDC (230 mg, 1.2 mmol) followed by the addition of isopropyl amine (130 μL, 1.5 mmol). After stirring at room temperature for 6 hours, the reaction mixture is treated with 1N HCl (10 mL) and ethyl acetate (30 mL). The organic layer is separated, washed with saturated $NaHCO_3$, dried over $Na_2SO_4$ and concentrated to provide isopropyl 4-N-BOC-1-N-FMOC-2-piperazine acetamide (4.2) (454.6 mg, 90%) as a white foam.

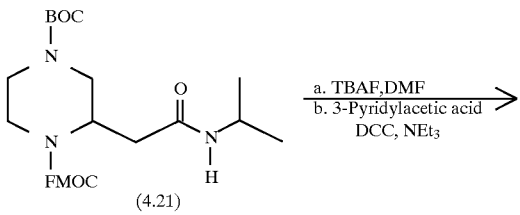

To the solution of isopropyl 4-N-BOC-1-N-FMOC-2-piperazine acetamide (4.2) (150 mg, 0.3 mmol) in DMF is added TBAF (142 mg, 0.45 mmol). After stirring at room temperature for ½ hour, the reaction mixture is treated with 1N HCl (5 mL) and ethyl acetate (10 ML). The aqueous layer is washed with ethyl acetate once, basified with saturated $K_2CO_3$ and extracted three times with ethyl acetate. The combined organic layers are dried over $MgSO_4$ and concentrated to afford the desired intermediate isopropyl-4-N-BOC-2-piperazine acetamide which is used for the following reaction without further purification. To the solution of 3-pyridylacetic acid (52 mg, 0.3 mmol) and triethyl amine (85 μL, 0.6 mmol) in 5 mL $CH_2Cl_2$ is added DCC (75 mg, 0.36 mmol) followed by the addition of isopropyl-4-N-BOC-2-piperazine acetamide in 2 mL $CH_2Cl_2$. The reaction mixture is stirred at room temperature for 8 hours and concentrated and purified by flash chromatography to give (5.1) (106.2 mg, 88%) as a colorless oil. $R_f$=0.4 (10% MeOH in $CH_2Cl_2$).

To a solution of (5.1) (0.1 g, 0.197 mmol) in DCM(6 mL) is added TFA (2 mL). The reaction mixture stirred at room temperature for one hour and is then evaporated to dryness in vacuo. The residue is dissolved in ethyl acetate (50 mL) and washed with water (40 mL). The aqueous phase is then basified with solid sodium carbonate and extracted with chloroform (5×20 mL). The organic phase is dried over $MgSO_4$ and concentrated in vacuo affording the deprotected material as an oil in mass 0.069 g (84%). To a solution of the oil (0.02 g, 0.07 mmol) in DCM (1 mL) is added DCC (0.021 g, 0.1 mmol) and 1-naphthoic acid (0.017 g, 0.1 mmole). The reaction mixture is stirred at room temperature for 8 hours and is then purified directly by flash chromatography ($SiO_2$, 5% methanol in DCM) affording (1.0) as an oil in mass 0.03 g (94%)

EXAMPLE 19

Preparation of 1

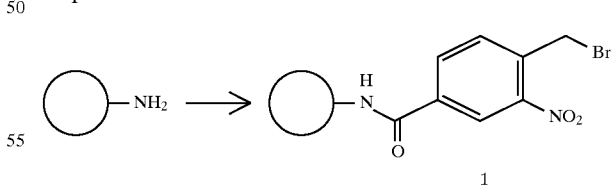

To a suspension of Tentagel S® $NH_2$ Resin (Rapp Polymere Gmbh, Germany) (1.0 g, 0.28 mmol/g loading, 0.28 mmol) in DCM (10 mL) in a Merrifield reaction vessel was added 4-(bromomethyl)-3-nitrobenzoic acid (1.12 mmol, 0.29 g), HOBT (1.12 mmol, 0.15 g) and DIC (1.68 mmol, 0.219, 0.26 mL). The resin shook at room temperature for 16h and was then washed with DCM (4×10 mL) and THF (3×10 mL).

Preparation of 2

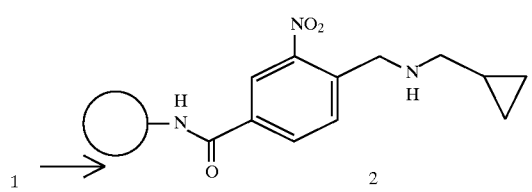

The resin (0.28 mmol theoretical loading) was suspended in THF (10 mL) and treated with (aminomethyl) cyclopropane (5.6 mmol, 0.40 g, 0.49 mL) at room temperature for 16h. The resin was then washed with THF (2×10 mL).

Preparation of 3

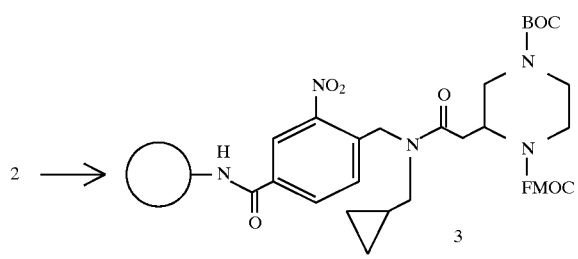

The resin (0.28 mmol theoretical loading) is suspended in DCM (10 mL) and reacted with 1-N-FMOC-4-BOC piperazine-2-acetic acid (1.12 mmol, 0.52 g), HATU (1.12 mmol, 0.43 g) and N,N-diisopropyethylamine (2.24 mmol, 0.29 g, 0.39 mL). The resin is shaken at room temperature for 16 h and is then washed with DCM (4×10 mL). The resin is then retreated with the same mixture of reagents in a second coupling cycle of 16 h. The resin is then washed with DCM (6×10 mL).

Preparation of 4

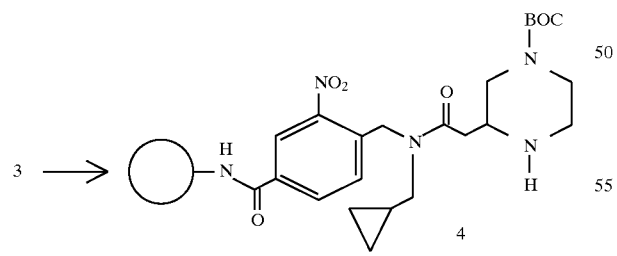

The resin (0.28 mmol theoretical loading) is washed once with DMF (10 mL) and is then treated with a 30% solution of piperidine in DMF (total volume=10 mL) at room temperature for 30 min. The resin is then washed with DMF (10 mL), methanol (2×10 mL) and DCM (3×10 mL).

Preparation of 5

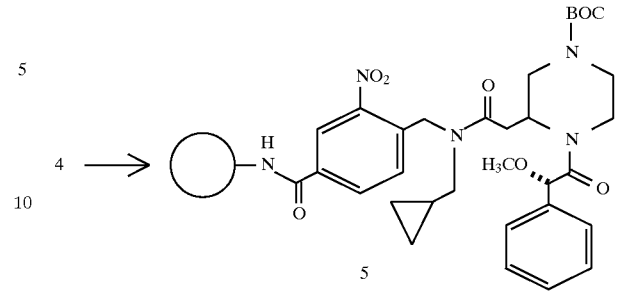

The resin (0.28 mmol theoretical loading) is suspended in DCM (10 mL) and treated with (S)-(+)-α-methoxyphenylacetic acid (1.12 mmol, 0.19 g), HATU (1.12 mmol, 0.43 g) and N,N-diisopropylethylamine (2.24 mmol, 0.29 g, 0.39 mL). The resin is shaken at room temperature for 16 h and then washed with DCM (4×10 mL).

Preparation of 6

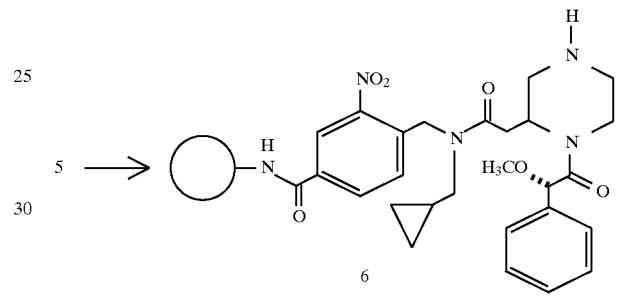

The resin (0.28 mmol theoretical loading) is treated with a 30% solution of TFA in DCM (10 mL) at room temperature for 1 h. The resin is then washed with DCM (2×10 mL) and methanol (3×10 mL) and then treated with a 20% solution of triethylamine in methanol (10 mL) for 30 min. The resin is then washed with methanol (2×10 mL) and DCM (4×10 mL).

Preparation of 7

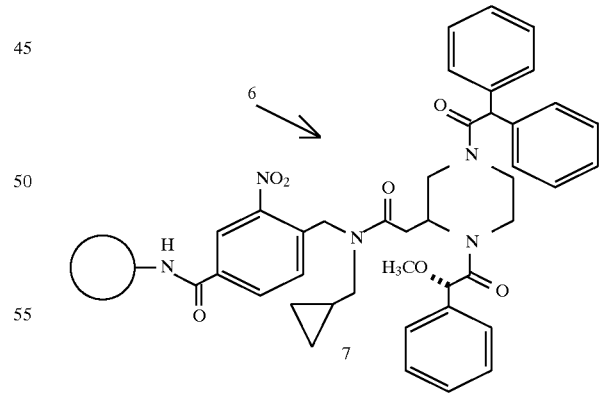

The resin (0.28 mmol theoretical loading) is suspended in DCM (10 mL) and treated with diphenylacetic acid (1.26 mmol, 0.27 g), HATU (1.26 mmol, 0.48 g) and N,N-diisopropylethylamine (2.52 mmol, 0.33 g, 0.44 mL). The resin is shaken at room temperature for 16 h and then washed with DCM (5×10 mL), DMF (3×10 mL) and methanol (3×10 mL).

Preparation of 8

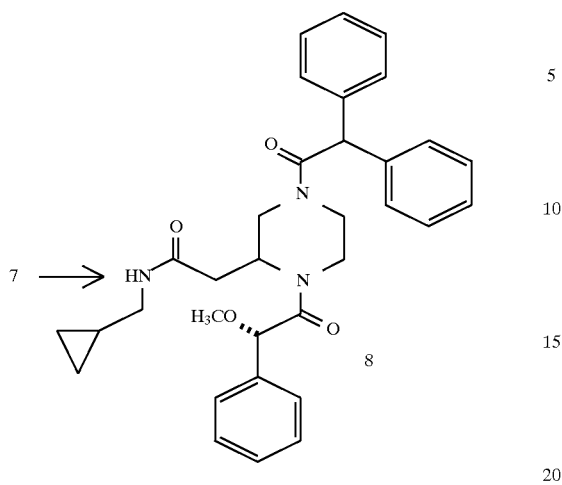

The resin (0.28 mmol theoretical loading) is washed from the Merrifield vessel into a 25 mL round-bottomed flask with methanol (10 mL) and photolysed (UVP Blak-Ray lamp, 360 nm) for 3 h. The resin is filtered and washed with methanol (3×10 mL) and DCM (3×10 mL). The solvent and washings are combined and evaporated to dryness in vacuo giving compound 8.

Representative $R^1$ groups in compounds (1.0) and (1.1) can include the following:

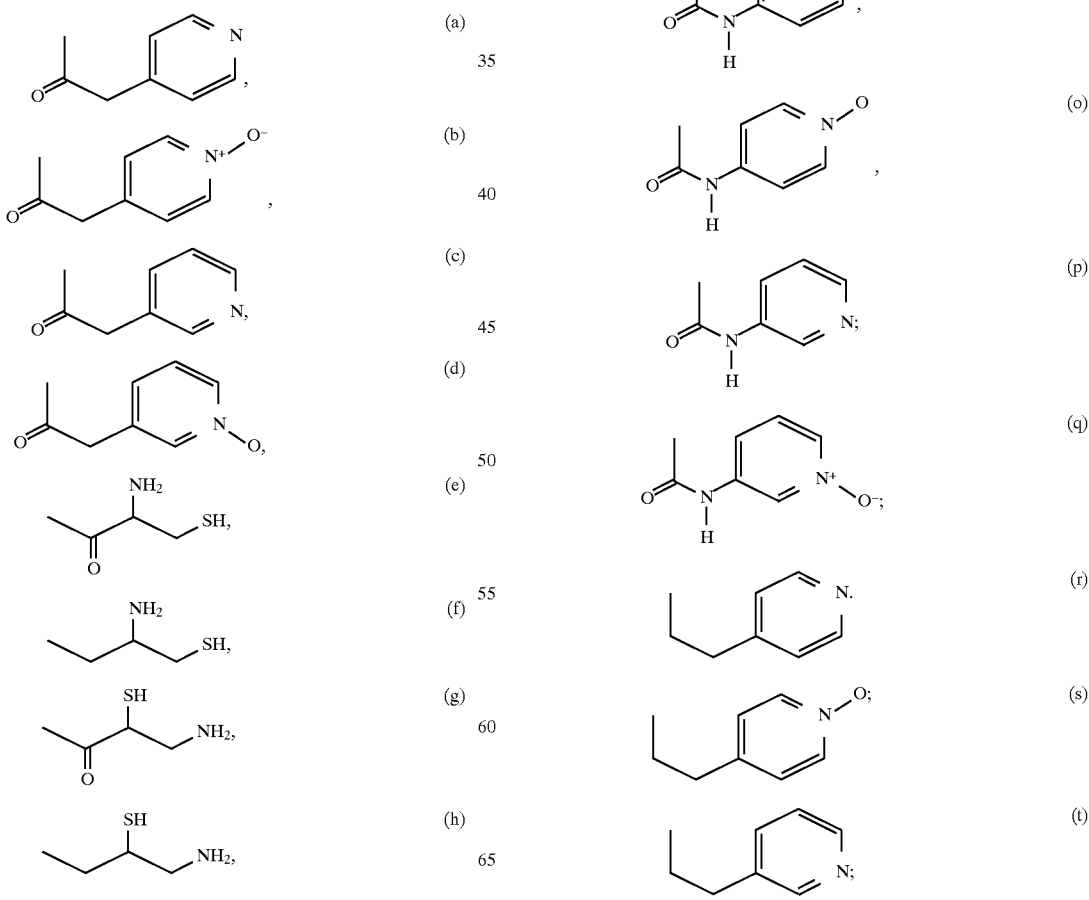

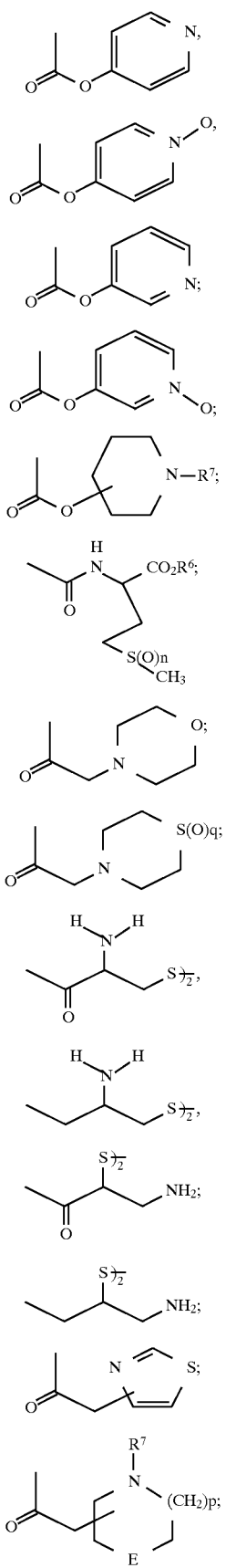
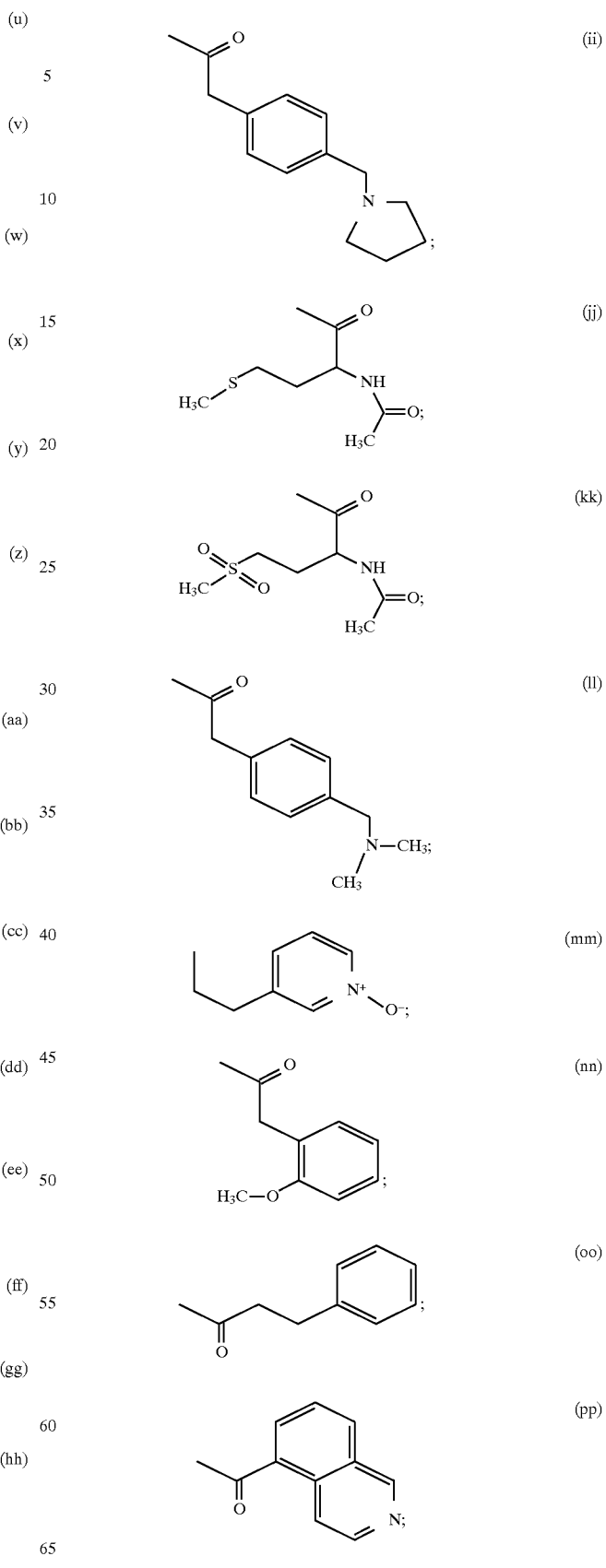

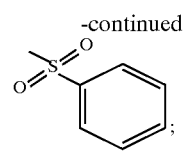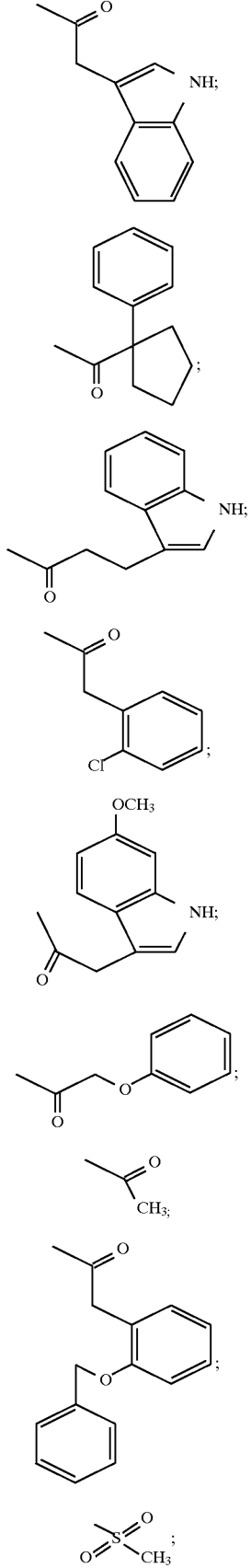

-continued

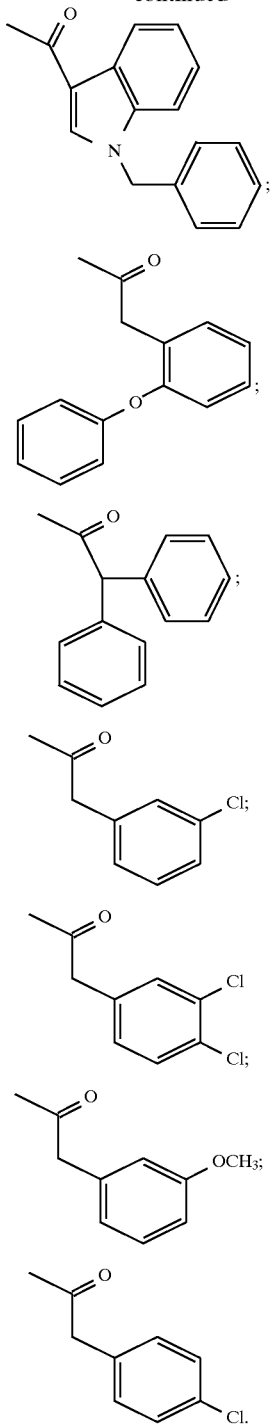

(iii)

(jjj)

(kkk)

(lll)

(mmm)

(nnn)

(ooo)

wherein p is 1 or 2;
q is 0, 1 or 2;
E is $CH_2$ or $NR^7$;
$R^6$ is H or $C_1$ to $C_6$ alkyl;
$R^7$ is H, $C_1$ to $C_6$ alkyl, haloalkyl, —C(O)$R^{11}$, —C(O)O$R^{13}$, —C(O)N$R^{14}R^{15}$ or an acyl radical of a naturally occuring amino acid; wherein
  $R^{11}$ is $C_1$ to $C_6$ alkyl, $C_1$ to $C_6$ alkoxy or —NH$R^{12}$ and
  $R^{12}$ is $C_1$ to $C_6$ alkyl or H;
with the proviso that when $X^1$ is N and $R^2$ is $C_1$ to $C_6$ alkyl or aralkyl, then $R^1$ is not (e) or (f).

Representative $R^2$ or $R^3$ groups in compounds (1.0) and (1.1) can include the following.

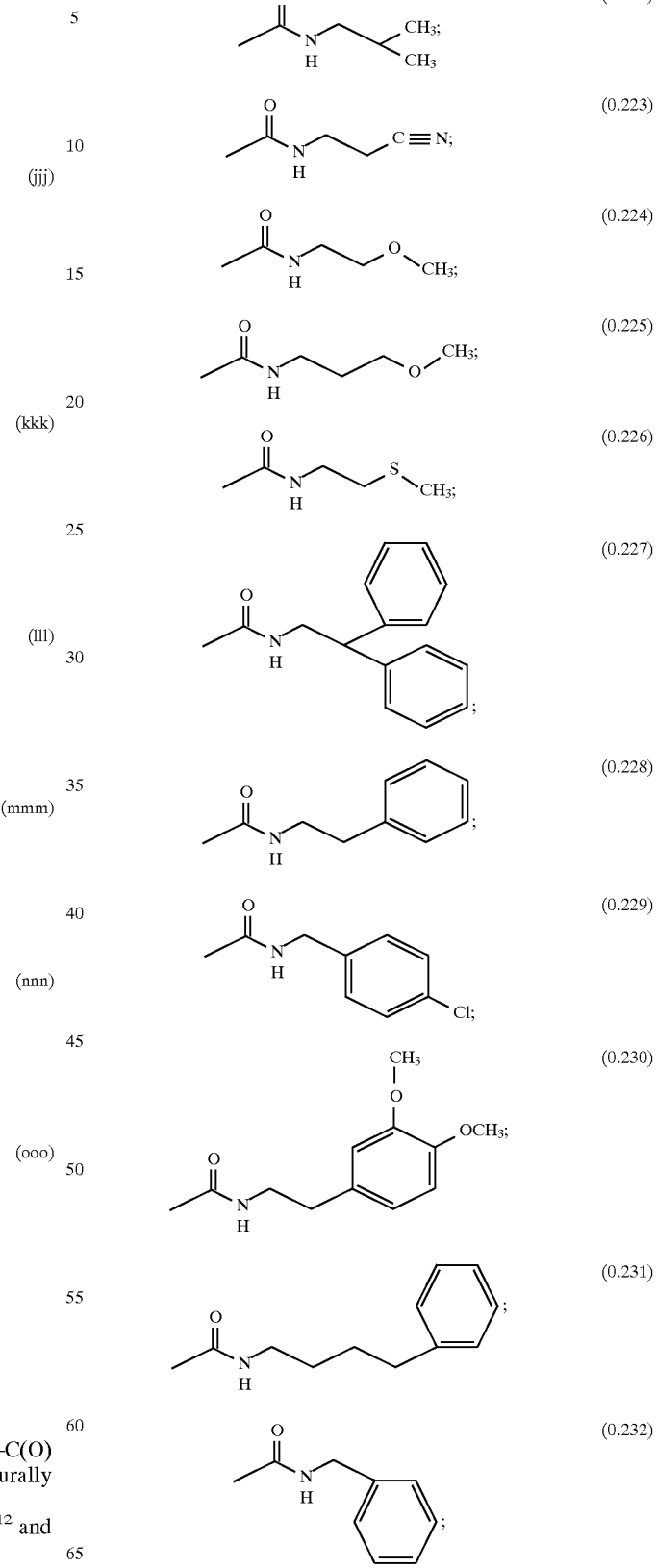

(0.222)
(0.223)
(0.224)
(0.225)
(0.226)
(0.227)
(0.228)
(0.229)
(0.230)
(0.231)
(0.232)

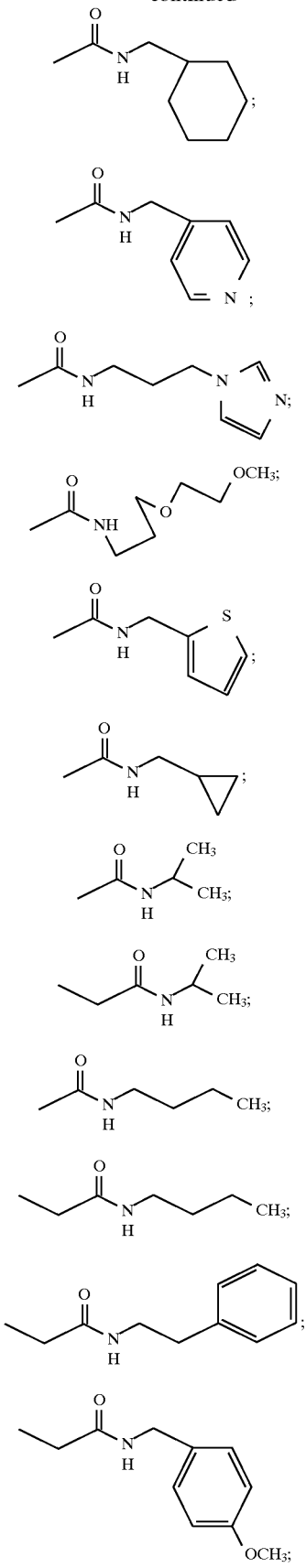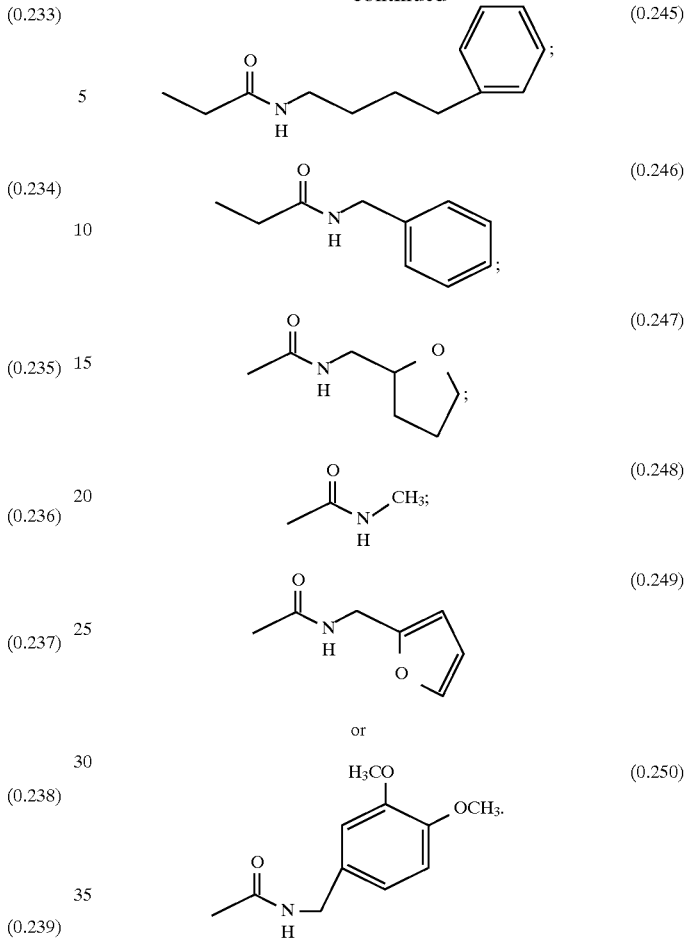

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable orally, or parenterally, including the intravenous, intramuscular, intraperitoneal, subcutaneous, rectal, transdermal and topical routes of administration. The transdermal compositions can take the form of creams, lotions, aerosols and/or emulsions and can be included in a transdermal patch of the matrix or reservoir type as are conventional in the art for this purpose. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

Tablets

| No. | Ingredients | mg/tablet | mg/tablet |
| --- | --- | --- | --- |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

Capsules

| No. | Ingredients | mg/capsule | mg/capsule |
| --- | --- | --- | --- |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine. While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Assays

Measurements of pharmacological activity of the present compounds can be made based upon a cell-based assay (i.e. FPT $IC_{50}$), cell mat assay (GGPT $IC_{50}$) or in vitro tumor activity (Cos Cell IC50) as described by the methods in WO95/10516.

The utility of the compounds of the present invention can be demonstrated by the following assay procedures.

1. In vitro enzyme assays: Inhibition of farnesyl protein transferase and geranylgeranyl protein transferase.

Both farnesyl protein transferase (FPT) and geranylgeranyl protein transferase (GGPT) I are partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, Proc. Natl. Acad. Sci USA 88: 5302–5306, the disclosure of which is incorporated herein by reference thereto). Human farnesyl protein transferase is also expressed in E. coli, using cDNA clones encoding both the α and β subunits. The methods used are similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase is partially-purified from the soluble protein fraction of E. coli as described above. The farnesyl protein transferase inhibitors disclosed herein may inhibit both human and rat enzyme with similar potencies. Two forms of $val^{12}$-Ha-Ras protein are prepared as substrates for these enzymes, differing in their carboxy terminal sequence. One form terminates in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I.

The cDNAs encoding these proteins are constructed so that the proteins contain an amino-terminal extension of 6 histidine residues. Both proteins are expressed in *Escherichia coli* and purified using metal chelate affinity chromatography. The radiolabelled isoprenyl pyrophosphate substrates, [$^3$H]farnesyl pyrophosphate and [$^3$H]geranylgeranyl pyrophosphate, are purchased from a commercial source, such as DuPont/New England Nuclear.

Several methods for measuring farnesyl protein transferase activity are known (Reiss et al 1990, Cell 62: 81; Schaber et al 1990, J. Biol. Chem. 265: 14701; Manne et al 1990, PNAS 8: 7541; and Barbacid & Manne 1993, U.S. Pat. No. 5,185,248). The activity is assayed by measuring the transfer of [$^3$H]farnesyl from [$^3$H]farnesyl pyrophosphate to Ras-CVLS using conditions similar to those described by Reiss et al., 1990 (Cell 62: 81) The reaction mixture contains 40 mM Hepes, pH 7.5; 20 mM magnesium chloride; 5 mM dithiothreitol; 0.25 $\mu$M [$^3$H]farnesyl pyrophosphate; 10 $\mu$l Q-Sepharose-purified farnesyl protein transferase; the indicated concentration of carbonyl piperazinyl or piperidinyl compound (1.0) or dimethylsulfoxide (DMSO) vehicle control (5% DMSO final); and 5 $\mu$M Ras-CVLS in a total volume of 100 $\mu$l. The reaction is allowed to proceed for 30 minutes at room temperature and then stopped with 0.5 ml of 4% sodium dodecyl sulfate (SDS) followed by 0.5 ml of cold 30% trichloracetic acid (TCA). Samples are allowed to sit on ice for 45 minutes and precipitated Ras protein is then collected on GF/C filter paper mats using a Brandel cell harvester. Filter mats are washed once with 6% TCA, 2% SDS and radioactivity is measured in a Wallac 1204 Betaplate BS liquid scintillation counter. Percent inhibition is calculated relative to the DMSO vehicle control.

The geranylgeranyl protein transferase I assay is essentially identical to the farnesyl protein transferase assay described above, with two exceptions: [$^3$H] geranylgeranylpyrophosphate replaces farnesyl pyrophosphate as the isoprenoid donor and Ras-CVLL is the protein acceptor. This is similar to the assay reported by Casey et al (Casey, P. J., et al., (1991), Enzymatic modification of proteins with a geranylgeranyl isoprenoid, Proc. Natl. Acad. Sci, USA 88: 8631–8635, the disclosure of which is incorporated herein by reference).

2. Cell-Based Assay: Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells are transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells are plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media is removed and fresh media containing the appropriate drugs is re-added.

48 hours after electroporation cells are examined under the microscope to monitor disordered cell growth induced by transforming Ras. Cells expressing transforming Ras become more rounded and refractile and overgrow the monolayer, reminiscent of the transformed phenotype. Cells are then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 $\mu$M leupeptin; and 0.1 $\mu$M pepstatin. Cells are lysed by homogenization and cell debris is removed by centrifugation at 2000×g for 10 min.

Cellular protein is precipitated by addition of ice-cold trichloroacetic acid and redissolved in 100 $\mu$l of SDS-electrophoresis sample buffer. Samples (5–10 $\mu$l) are loaded onto 14% polyacrylamide minigels (Novex, Inc.) and electrophoresed until the tracking dye neared the bottom of the gel. Proteins resolved on the gels are electroblotted onto nitrocellulose membranes for immunodetection.

Membranes are blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the P21 products of the transforming gene of Harvey murine sarcoma virus and of the cellular ras gene family, J. Virol. 43: 294–304), in PBS containing 1% fetal calf serum for one hour at room temperature. After washing, membranes are incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL is detected using a colorimetric peroxidase reagent (4-chloro-1-naphthol) as described by the manufacturer (Bio-Rad).

3. Cell Mat Assay:

Normal human HEPM fibroblasts are planted in 3.5 cm dishes at a density of 5×10$^4$ cells/dish in 2 ml growth medium, and incubated for 3–5 d to achieve confluence. Medium is aspirated from each dish and the indicator tumor cells, T24-BAG4 human bladder carcinoma cells expressing an activated H-ras gene, are planted on top of the fibroblast monolayer at a density of 2×10$^3$cells/dish in 2 ml growth medium, and allowed to attach overnight. Compound-induced colony inhibition is assayed by addition of serial dilutions of compound directly to the growth medium 24 h after tumor cell planting, and incubating cells for an additional 14 d to allow colony formation. Assays are terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci. 84, 156–160(1987)). In the colony inhibition assay, compounds are evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values are obtained by determining the density of tumor cells and mat cells by visual inspection and enumeration of cells per colony and the number of colonies under the microscope. The therapeutic index of the compound is quantitatively expressed as the ratio of mIC$_{50}$/tIC$_{50}$, with values greater than one indicative of tumor target specificity.

Under the test protocols employed, there were certain compounds within the scope of the present invention which did not exhibit activity. It is believed that such compounds would exhibit activity under a different test protocol.

The following compounds exhibited biological activity at concentrations below 10 micromoles (um) using an in vitro assay measuring the inhibition of FTase.

| Ex. No. | Z | R¹ | R² |
|---|---|---|---|
| 21 | diphenylmethyl (CHPh₂, with CH₃) | 1-naphthylsulfonyl | acetyl-NH-CH₃ |
| 22 | diphenylmethyl | 2-oxo-1-(4-benzyloxyphenyl)ethyl | acetyl-NH-cyclopropyl |
| 23 | diphenylmethyl | 2-oxo-1-methoxy-1-phenylethyl | propanoyl-NH-CH₂-cyclopropyl |
| 24 | diphenylmethyl | 1-naphthylsulfonyl | acetyl-NH-CH₂-cyclopropyl |
| 25 | diphenylmethyl | 2-oxo-1-(pyridin-3-yl)ethyl | acetyl-NH-CH₂-cyclopropyl |
| 26 | diphenylmethyl | 2-oxo-1-methoxy-1-phenylethyl | acetyl-NH-CH(CH₃)₂ |
| 27 | diphenylmethyl | benzylsulfonyl | propanoyl-NH-CH(CH₃)₂ |

-continued
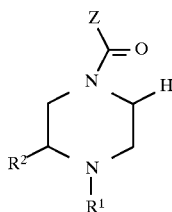 (1.0)
| Ex. No. | Z | R¹ | R² |
|---|---|---|---|
| 28 | 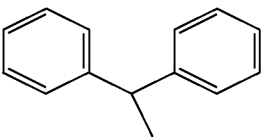 | 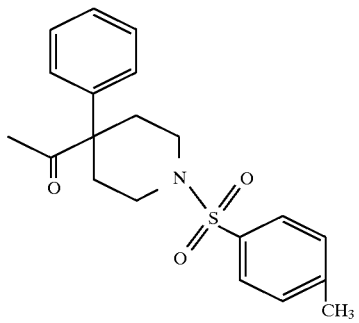 | 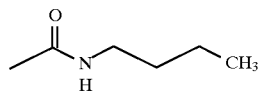 |
| 29 | 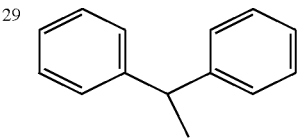 | 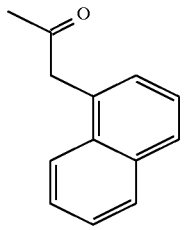 | 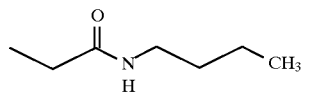 |
| 30 | 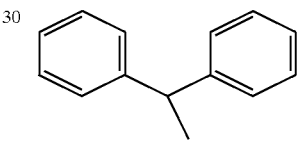 | 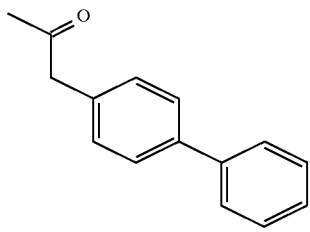 | 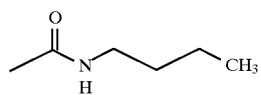 |
| 31 | 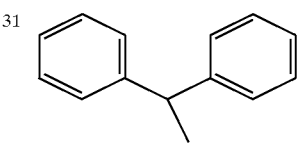 | 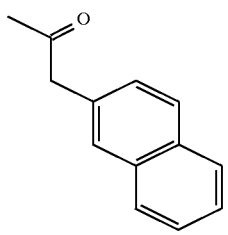 | 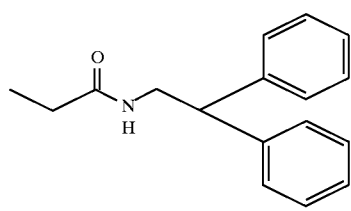 |
| 32 | 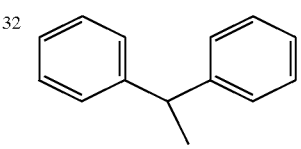 | 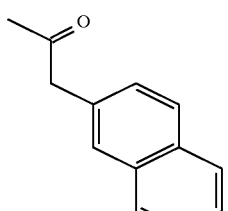 | 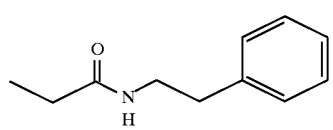 |

-continued
$$\text{(1.0)}$$
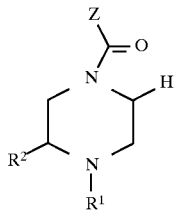
| Ex. No. | Z | R¹ | R² |
|---|---|---|---|
| 33 | 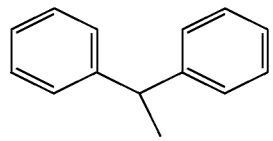 | 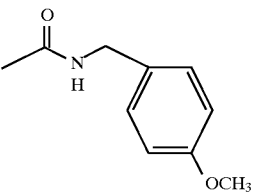 | 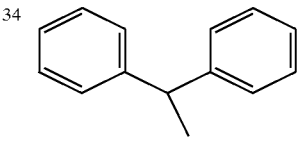 |
| 34 | 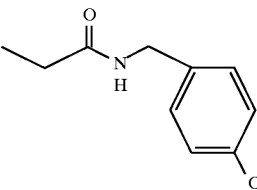 | 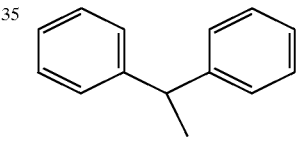 | 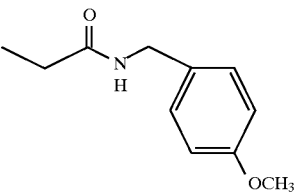 |
| 35 | 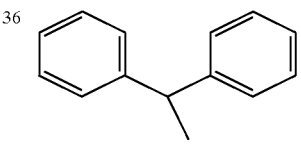 | 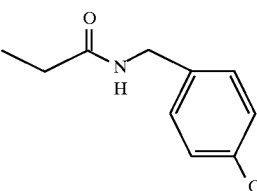 | 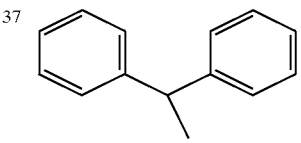 |
| 36 | 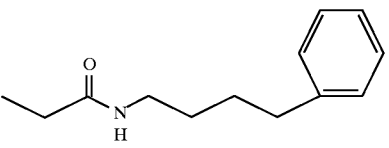 | 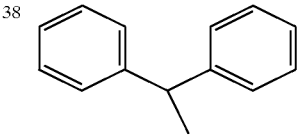 | 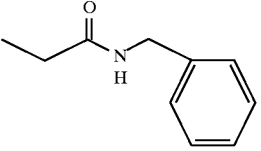 |
| 37 | 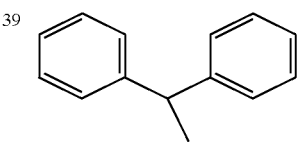 | | |
| 38 | | | |
| 39 | | 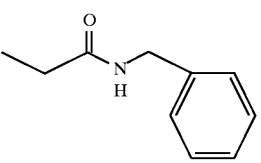 | |

-continued
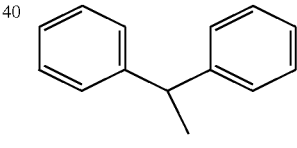
| Ex. No. | Z | R[1] | R[2] |
| --- | --- | --- | --- |
| 40 | 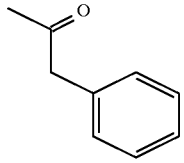 | 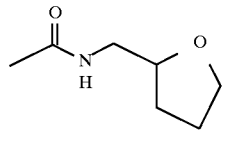 | 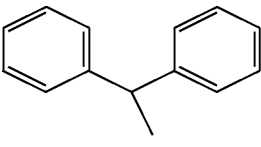 |
| 41 | 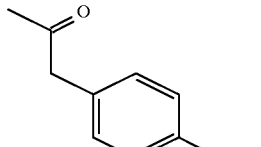 | 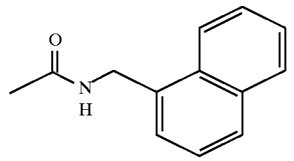 | 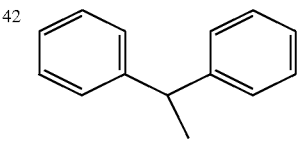 |
| 42 | 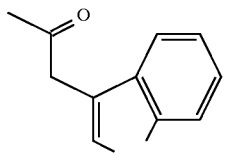 | 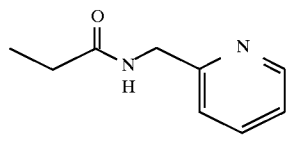 | 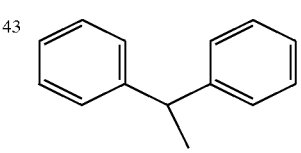 |
| 43 | 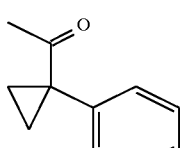 | 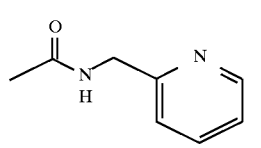 | 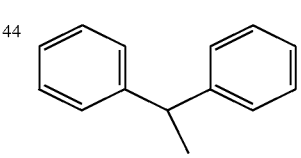 |
| 44 | 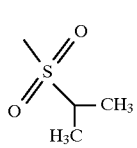 | 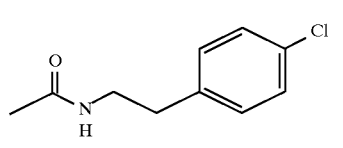 | 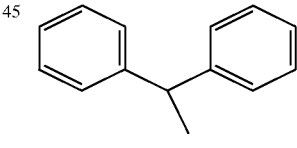 |
| 45 | 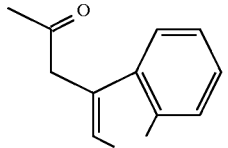 | 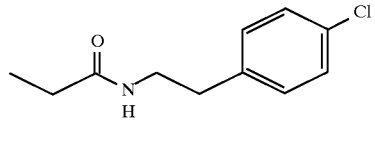 | 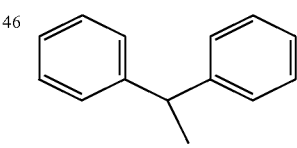 |
| 46 | 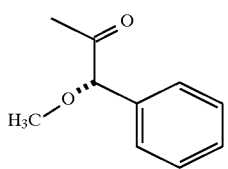 | 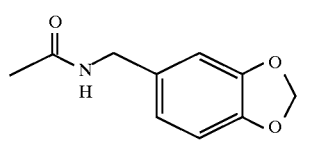 | |

-continued
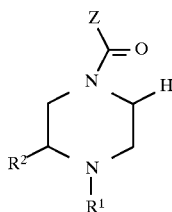 (1.0)
| Ex. No. | Z | R¹ | R² |
|---|---|---|---|
| 47 | 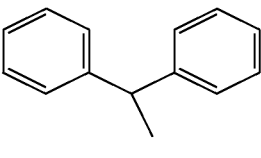 | 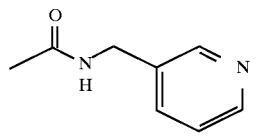 | 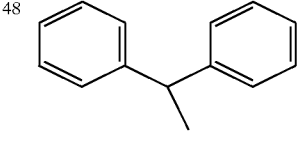 |
| 48 | 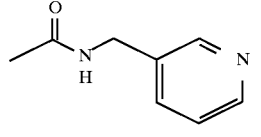 | 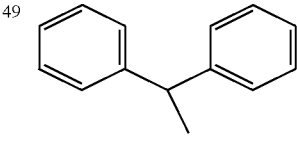 | 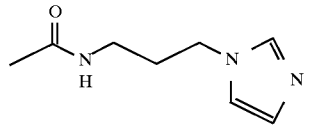 |
| 49 | 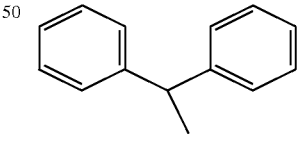 | 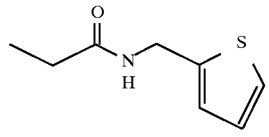 | 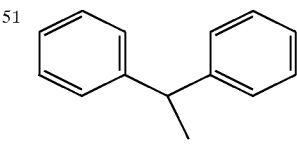 |
| 50 | 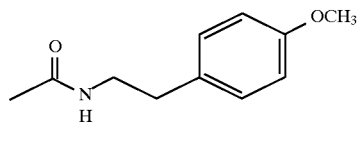 | | |
| 51 | | | |

-continued
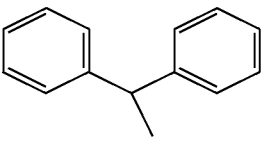 (1.0)
| Ex. No. | Z | R[1] | R[2] |
|---|---|---|---|
| 52 | 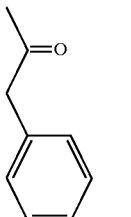 | 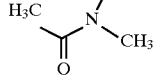 | 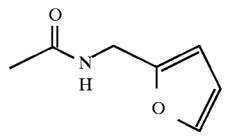 |
| 53 | 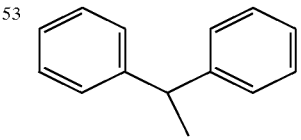 | 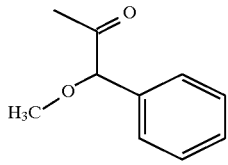 | 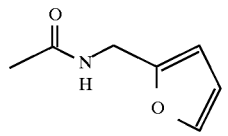 |
| 54 | 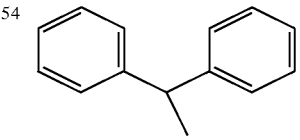 | 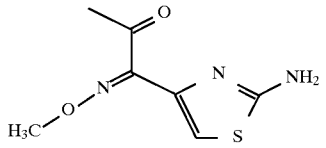 | 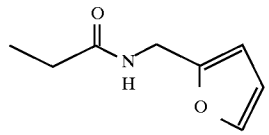 |
| 55 | 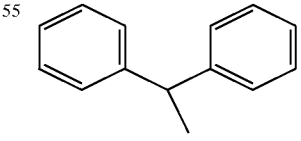 | 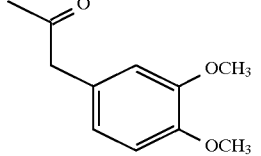 | 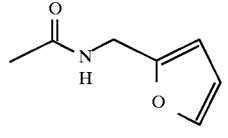 |
| 56 | 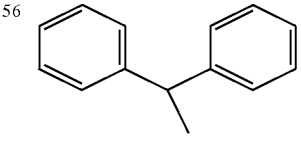 | 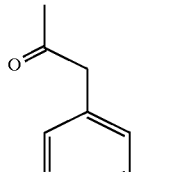 |  |

-continued
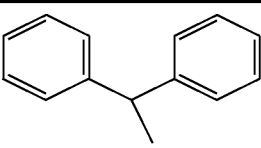 (1.0)
| Ex. No. | Z | R¹ | R² |
|---|---|---|---|
| 57 | 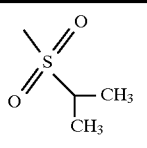 | 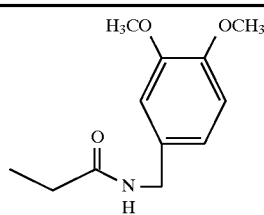 | 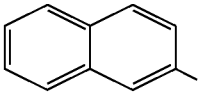 |
FPT IC$_{50}$ values refer to concentration, in micromoles (μM), of compound which inhibits 50% of FPT transferase.
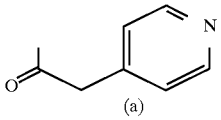 (1.0)
wherein R³ = H
| Z | X¹ | R¹ | R² | FPT IC$_{50}$ (μM) |
|---|---|---|---|---|
| 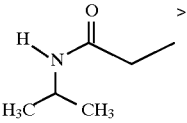 | N | 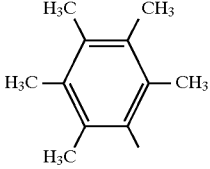 (a) | 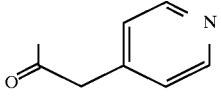 | >50 |
| 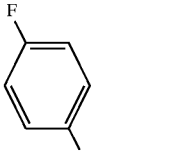 | CH | 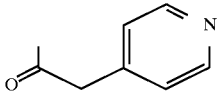 | H | 12.1 |
| 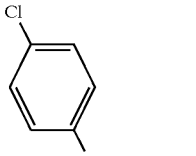 | CH | 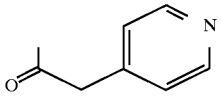 | H | >60 |
| Cl-⌬- | CH | (pyridyl-CH₂-CO-) | H | 60 |

-continued

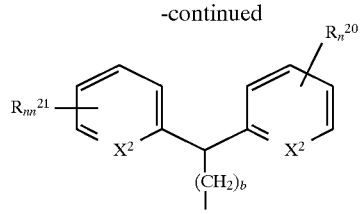

| Z | X¹ | R¹ | R² | FPT IC$_{50}$ ($\mu$M) |
|---|----|----|----|------------------------|
| [phenyl] | CH | [pyridin-4-ylmethyl ketone] | H | >60 |

What is claimed is:

1. A compound of the formula:

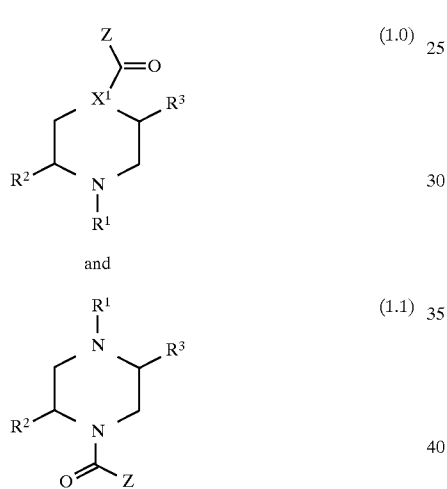

or a pharmaceutically acceptable salt or solvate thereof, wherein:

(1) Z is a group which is:

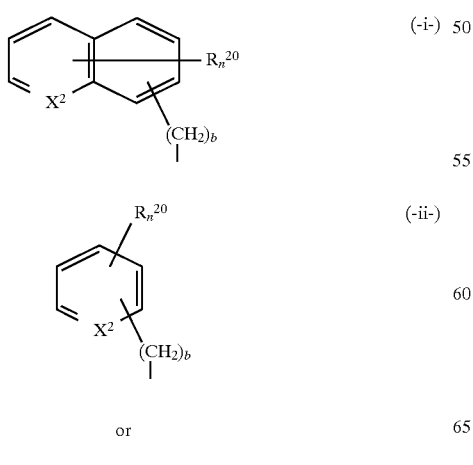

wherein $X^1$ is N;
$X^2$ can be the same or different and can be N or N—O;
b is 0, 1, 2, 3 or 4;
n and nn independently represent 0, 1, 2, 3, 4;
$R^{20}$ and $R^{21}$ can be the same group or different groups when n or nn is 2, 3, 4 or 5, and can be:
(a) hydrogen, $C_1$ to $C_6$ alkyl, aryl, aralkyl, heteroaryl, heteroarylalkyl or heterocycloalkyl, wherein each of said $C_1$ to $C_6$ alkyl, aryl, aralkyl, heteroaryl, heteroarylalkyl or heterocycloalkyl can be optionally substituted with one or more of the following:
$C_1$ to $C_4$ alkyl, $C_3$–$C_6$ cycloalkyl, $(CH_2)_tOR^8$ wherein t is 0, 1, 2, 3 or 4, $(CH_2)_tNR^8R^9$ wherein t is 0, 1, 2, 3 or 4, or halogen;
(b) $C_3$ to $C_6$ (c) —$OR^8$; (d) —$SR^8$; (e) —$S(O)R^8$; cycloalkyl; (f) —$SO_2R^8$; (g) —$NR^8R^9$; (h) —CN; (i) —$NO_2$, (j) —$CF_3$ or (k) halogen (l) —$CONR^8R^9$ or (m) —$COR^{13}$
wherein $R^8$ and $R^9$ can independently represent:
H, $C_1$ to $C_4$ alkyl, $C_3$ to $C_6$ cycloalkyl, heteroaryl, heteroarylalkyl, heterocycloalkyl, aryl or aralkyl and each of said alkyl, cycloalkyl, heteroaryl, heteroarylalkyl, heterocycloalkyl, aryl or aralkyl can be optionally substituted with one to three of the following:
$C_1$ to $C_4$ alkoxy, aryl, aralkyl, heteroaryl, heteroarylalkyl, heterocycloalkyl, halogen, —OH, —$C(O)R^{13}$, —$NR^{14}R^{15}$; —$CONR^8R^9$ or —$N(R^8)COR^{13}$; —CN; $C_3$–$C_6$ cycloalkyl, $S(O)_qR^{13}$;
or $C_3$–$C_{10}$ alkoxyalkoxy wherein q is 0, 1 or 2; wherein $R^{13}$ is selected from $C_1$ to $C_4$ alkyl, aryl or aralkyl, and
$R^{14}$ and $R^{15}$ are independently selected from H, $C_1$ to $C_4$ alkyl or aralkyl;
and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, $S(O)q$ wherein q is 0, 1 or 2;

with the proviso that $R^8$ is not H in substituents (e) and (f), and with the proviso that $R^8$ or $R^9$ is not —$CH_2OH$ or —$CH_2NR^{14}R^{15}$ when $R^8$ or $R^9$ is directly attached to a heteroatom;

(2) $R^1$ is a group which is:

$$-T-\left[\begin{array}{c}R^a\\|\\C\\|\\R^b\end{array}\right]_x-R^{10}$$

wherein
T can be $$-\overset{O}{\overset{\|}{C}}-,\ -SO_2-,\ -\overset{O}{\overset{\|}{C}}-NH-,\ -\overset{O}{\overset{\|}{C}}-O-,$$

or a single bond, x=0, 1, 2, 3, 4, 5 or 6, $R^a$ and $R^b$ independently represent H, aryl, alkyl, amino, alkylamino, alkoxy, aralkyl, heterocyloalkyl, —$COOR^{16}$, —$NH(CO)_zR^{16}$ wherein z=0 or 1, —$(CH_2)_wS(O)_mR^{16}$ wherein w=0, 1, 2 or 3 such that when x is greater than 1, then $R^a$ and $R^b$ can be independent of the substituents on an adjacent carbon atom provided $R^a$ and $R^b$ are not both selected from alkoxy, amino, alkylamino, and —$NH(CO)_zR^{16}$;

m=1 or 2 wherein $R^{16}$ represent H, alkyl, aryl or aralkyl, or $R^a$ and $R^b$ taken together can represent cycloalkyl, =O, =N—O-alkyl or heterocycloalkyl, and $R^{10}$ can represent H, alkyl, aryl, aryloxy, arylthio, aralkoxy, aralkthio, aralkyl, heteroaryl, heterocycloalkyl, (3) $R^2$ and $R^3$ are independently selected from the group which is:

hydrogen, $C_1$ to $C_8$ alkyl, $C_2$ to $C_8$ alkenyl, $C_2$ to $C_8$ alkynyl, $$-(CH_2)_z\underset{O}{\overset{}{\diagdown}}NR^8R^9 \quad \text{or} \quad -(CH_2)_z\underset{O}{\overset{}{\diagdown}}OR^8;$$

wherein z is 0, 1, 2, 3 or 4; and said alkyl, alkenyl, or alkynyl group is optionally substituted with one or more groups which can independently represent:

(a) aryl, aralkyl, heteroaryl, heteroarylalkyl or heterocycloalkyl, wherein each of said aryl, aralkyl, heteroaryl, heteroarylalkyl or heterocycloalkyl group can be optionally substituted with one or more of the following:

$C_1$ to $C_4$ alkyl, $(CH_2)_tOR^8$ wherein t is 0, 1, 2, 3 or 4, $(CH_2)_tNR^8R^9$ wherein t is 0, 1, 2, 3 or 4, or halogen;

(b) $C_3$ to $C_6$ (c) —$OR^8$; (d) —$SR^8$; (e) —$S(O)R^8$; cycloalkyl; (f) —$SO_2R^8$; (g) —$NR^8R^9$;

(h) $-\overset{R^8}{\underset{\overset{\|}{O}}{N}}-\overset{}{C}-R^9$; (i) $-\overset{R^8}{\underset{\overset{\|}{O}}{N}}-\overset{}{C}-NR^8R^9$ (j) $-O-\overset{}{\underset{\overset{\|}{O}}{C}}-NR^8R^9$;

(k) $-O-\overset{}{\underset{\overset{\|}{O}}{C}}-OR^8$; (l) $-\overset{}{\underset{\overset{\|}{O}}{C}}-NR^8R^9$; (m) $-SO_2-NR^8R^9$ (n) $-\overset{R^8}{\underset{}{N}}-SO_2-R^9$ (o) $\overset{}{\underset{\overset{\|}{O}}{C}}-OR^8$ or (p) $-\overset{R^8}{\underset{}{N}}-SO_2-NR^8R^9$ wherein $R^8$ and $R^9$ are defined hereinbefore; and and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, $S(O)q$ wherein q is 0, 1 or 2;

and with the provision that when $X^1$ is N, then $R^1$ is not

[structures: $NH_2$-substituted ketone with SH; $NH_2$-substituted with SH; pyridylmethyl structures]

and with the further proviso that $R^1$ does not contain an amino mercaptyl group.

2. The compound of claim 1 wherein $R^3$ is hydrogen.
3. The compound of claim 1 wherein b is zero.
4. The compound of claim 1 wherein $R^3$ is H and b is 0.
5. The compound of claim 1 wherein Z is (—i—), (—ii—) or (—iii—), $X^2$ is N, b=0 or 1, $R^{20}$ is H, C1–C6 alkyl or halo, n=0 or 1;

$X^1$ is N;

for $R^1$, T is —CO—, —$SO_2$— or a single bond, and $R^a$ and $R^b$ independently represent H or $C_1$–$C_6$ alkoxy or $R^a$ and $R^b$ taken together can form $C_3$–$C_6$ C1–C6 alkyl or

[structure: cyclohexyl–SO2–phenyl–CH3]

cycloalkyl, =N—O—

$R^{10}$ is H, aryl, arylthio or heteroaryl;

$R^2$ is H, $$-(CH_2)_z\underset{O}{\overset{}{\diagdown}}NR^8R^9 \quad \text{or} \quad -(CH_2)_z\underset{O}{\overset{}{\diagdown}}OR^8$$

z=0 or 1, $R^8$ is H and $R^9$ is alkyl, cycloalkyl, aralkyl, heterocycloalkyl or substituted alkyl; and $R^3$ is hydrogen.

6. A pharmaceutical composition for inhibiting the abnormal growth of cells comprising an effective amount of compound of claim 1 in combination with a pharmaceutically acceptable carrier.

7. A method for inhibiting the abnormal growth of cells comprising administering an effective amount of a compound of claim 1.

8. The method of claim 7 wherein the the cells inhibited are tumor cells expressing an activated ras oncogene.

9. The method of claim 7 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

10. The method of claim 7 wherein the inhibition of the abnormal growth of cells occurs by the inhibition of ras farnesyl protein transferase.

11. The method of claim 7 wherein the inhibition is of tumor cells wherein the Ras protein is activated as a result of oncogenic mutation in genes other than the Ras gene.

* * * * *